United States Patent [19]
Nakanishi et al.

[11] Patent Number: 5,818,058
[45] Date of Patent: Oct. 6, 1998

[54] PARTICLE BEAM IRRADIATION APPARATUS

[75] Inventors: Tetsuya Nakanishi; Shinji Sato; Akihiko Maruyama; Tetsuya Matsuda; Chihiro Tsukishima; Hirofumi Tanaka, all of Tokyo, Japan

[73] Assignee: Mitsubishi Denki Kabushiki Kaisha, Tokyo, Japan

[21] Appl. No.: 785,257

[22] Filed: Jan. 17, 1997

[30] Foreign Application Priority Data

Jan. 18, 1996 [JP] Japan ..................................... 8-006457

[51] Int. Cl.⁶ .............................. A61N 5/00; H01J 37/147
[52] U.S. Cl. ........................ 250/492.3; 376/112; 315/502
[58] Field of Search ......................... 250/492.3; 376/112; 315/502

[56] References Cited

U.S. PATENT DOCUMENTS

| 4,112,306 | 9/1978 | Nunan ..................................... 376/112 |
| 4,641,104 | 2/1987 | Blosser et al. .......................... 376/112 |
| 5,349,198 | 9/1994 | Takanaka ............................. 250/492.3 |

OTHER PUBLICATIONS

Blosser, Nuclear Instruments and Methods in Physics Research B40–41(1989) 1326, 1328 (pp. 1327 and 1329–1330 missing).

"The Davis 76–inch Isochronous Cyclotron", Crocker Nuclear Laboratory.

Flanz et al., "The Northeast Proton Therapy Center at Massachusettes General Hospital" (Contributed paper to Fifth Workshop on Heavy Charge Particles in Biology and Medicaine) cited in the specification, Aug., 1995.

Flanz, "Large Medical Gantries" (1995 Particle Accelerator Conference).

Blosser "Applications of Superconduction Cyclotrons" (Twelfth International Conference on Cyclotrons and Their Applications) cited in the soecification.

*Primary Examiner*—Jack I. Berman
*Attorney, Agent, or Firm*—Sughrue, Mion, Zinn, Macpeak & Seas, PLLC

[57] ABSTRACT

An acceleration orbit face of particle beam circular acceleration unit is placed at right angles to a rotation shaft of rotation unit for rotating the particle beam circular acceleration unit, beam transport unit, and irradiation field formation unit in one piece. Shields for shielding radiations and magnetism are placed symmetrically with respect to the center axis of the particle beam circular acceleration unit. Shields are placed symmetrically with respect to the center line of the particle beam circular acceleration means, thereby lessening the amount of beams coming in collision with surrounding walls from the beam acceleration orbit, decreasing the radiation leakage amount, lightening the shields, and providing a light particle beam irradiation apparatus.

23 Claims, 17 Drawing Sheets

D: DIPOLE
Q: QUAD
S: SLIT

PARTICLE BEAM IRRADIATION APPARATUS

BACKGROUND OF THE INVENTION

This invention relates to a particle beam irradiation apparatus for accelerating a particle beam such as a proton beam to high energy and irradiating a carcinoma tissue of a human body for destroying the carcinoma tissue and more particularly to a rotary particle beam irradiation apparatus having an irradiation section rotated for irradiation.

A conventional rotary particle beam irradiation apparatus has a general structure shown in FIGS. 23 and 24, for example, shown in "The Fifth Workshop on Heavy Charge Particle in Biology and Medicine". FIG. 23 shows a general view of the irradiation apparatus and FIG. 24 shows an example of a rotary irradiation bed of an irradiation part. In the figures, numeral 1 is a cyclotron as a particle beam circular acceleration means for generating a particle beam such as a proton beam and accelerating it to high energy, numeral 2 is quadrupole electromagnets for focusing a particle beam of a collection of high-speed particles to any desired form, numeral 3 is deflection electromagnets for deflecting a particle beam, numeral 4 is diverting electromagnets for diverting the transport direction of a particle beam, and numeral 5 is a rotary particle beam irradiation unit for irradiating a target of a cancer patient with a particle beam. Numeral 6 is an irradiation field formation unit for irradiating a target with a particle beam, numeral 7 is a treatment bed on which a patient is placed, numeral 8 is a rotation frame for supporting an irradiation part rotating for irradiating with a particle beam, and numeral 9 is a rotation drive for driving the rotation frame 8. Numeral 10 is a rotation roller for receiving the rotation frame 8. Numeral 11 is a counter weight for balancing the weight of the rotation frame 8. Numeral 12 is a coupling beam for coupling the two rotation frames 8.

According to the particle beam irradiation apparatus thus configured, charged particles produced in the center of the cyclotron 1 in a magnetic field are rotated and accelerated to form a particle beam. The particle beam is focused and deflected by means of the quadrupole electromagnets 2, the deflection electromagnets 3, and the diverting electromagnets 4 properly placed in beam transport means, then transported for irradiating an irradiated body on the rotary irradiation unit 5 shown in FIG. 24 with the beam. The rotary irradiation unit 5 has the treatment bed 7 placed at the center of rotation of the rotary irradiation unit 5. To irradiate an irradiated body placed on the treatment bed 7 with a particle beam in a direction at right angles to the irradiated body, beam transport means for deflecting the particle beam in the direction at right angles to the irradiated body and guiding the resultant particle beam and the irradiation field formation unit 6 for forming an irradiation field conforming to the irradiated body are placed between a pair of rotation frames 8. The counter weight 11 is attached to the rotation irradiation unit 5 for balancing the weight of the rotation body. The rotation frames 8 are received by their respective rollers 10 for rotation and can be rotated by the rotation drive 9 for irradiation. The orbital path of a particle beam is formed in a vacuum chamber. The end of the vacuum chamber at the connection part to the irradiation part is sealed with a thin film placed facing the irradiation part.

In the particle beam irradiation apparatus, the irradiation part rotates about an irradiated body as shown in FIG. 24, a particle beam proceeds along the orbital path indicated by the alternate long and short dash line in the figure, and the part entering the rotary irradiation part is on the center line of rotation and becomes an orbital path of the beam. The vacuum chamber is sealed with a thin film facing the irradiation part and the particle beam makes a short-distance flight in the air in this part.

In the particle beam irradiation apparatus thus configured, only the irradiation part is rotated and particle beam generation and acceleration means are fixed, so that a large space is required on the whole, but the irradiation part is comparatively light and rotates easily.

A rotary particle beam irradiation apparatus shown in FIG. 25 shown in TWELFTH INTERNATIONAL CONFERENCE ON CYCLOTRONS AND THEYER APPLICATIONS is available as an example of a rotary particle beam irradiation apparatus more compact than the conventional one. In FIG. 25, numeral 20 is a cyclotron placed transversely, numeral 21 is a bearing, numeral 22 is a rotation support frame to which the cyclotron 20 and particle beam focusing and deflection means are attached for rotation, numeral 23 is a quadrupole electromagnet for focusing a particle beam, numeral 24 is a deflection electromagnet for deflecting the beam direction, numeral 25 is a beam transport line for defining a particle beam transport passage, numeral 26 is an irradiation field formation unit for irradiating a target with a particle beam, numeral 27 is a treatment bed, and numeral 28 is a radiation protection plate being placed between the cyclotron 20 and an irradiation chamber and having a magnetic shielding capability for shielding a magnetic field leaked from the cyclotron 20 and a radiation generated from the cyclotron 20. The radiation protection plate 28 is fixed to the rotation support frame 22. Numeral 29 is radiation protection walls surrounding the cyclotron 20 and a treatment chamber and numeral 30 is a roller for rotatably supporting the rotation support frame 22.

In the configuration, the cyclotron 20 for generating and accelerating a particle beam rotates and the beam transport means 25 for defining a passage of the particle beam accelerated and emitted by the cyclotron 20 and the irradiation field formation unit 26 can rotate in one piece for irradiating a target at varied angles with the particle beam. The radiation protection plate 28 disposed between the cyclotron 20 and the irradiation field formation unit 26 is circular and is attached to the rotation support frame 22 for shielding the entry of a neutron beam emitted from the cyclotron 20 into the irradiation chamber.

FIG. 26 is a schematic drawing to show the configuration of the cyclotron. FIG. 27 illustrates operation principles of the cyclotron in FIG. 26 and is a principle drawing to show how particles are accelerated and taken out. In the figures, numeral 31 is an ion source, numeral 32 is a dee electrode, numeral 33 is a vacuum vessel for accommodating the ion source 31 and the dee electrode 32 and is maintained under vacuum, numeral 34 is a pair of magnetic coils being placed on both sides of the vacuum vessel 33 accommodating the ion source 31 and the dee electrode 32 for generating a magnetic field, and numeral 35 is a yoke for locking a magnetic flux into the center. Numeral 36 is a deflector for deflecting an accelerated particle beam in a direction of emitting the beam, numeral 37 is a high frequency power supply, and numeral 38 is an acceleration orbit of a particle beam.

As shown in FIG. 27, the cyclotron is placed with the dee electrodes 32 and the ion source 31 as the center and is divided into front and rear parts with a predetermined space held at the center. A high-frequency voltage is applied between the front and rear dee electrodes 32 and a particle beam is accelerated and spreads to the outer peripheral surface in sequence like the particle beam orbit 38 and is deflected in the outer peripheral direction by the deflector, then emitted. The accelerated and emitted particle beam is focused by means of the quadrupole 23 in FIG. 25, is deflected by means of the deflection electromagnet 24 in a predetermined direction, is guided to the beam transport line 25, and is applied to an irradiated body by the irradiation field formation unit 6 or 26.

In FIG. 23, the irradiation part (the part shown in FIG. 24) rotates about an irradiated body and the target can be irradiated with a particle beam at any desired angle in the range in which the irradiation part can rotate. In FIG. 25, the irradiation part containing the cyclotron 20 can rotate about the target, and the target can be irradiated with a particle beam at any desired angle in the range in which the irradiation part can rotate as with the system in FIG. 23.

The configuration enables organs within a particle beam to be skipped when cancer cells are irradiated with a particle beam. If irradiation is executed a large number of times, the irradiation angle can also be changed each time irradiation is executed. Thus, the irradiation amount of cancer cells can be increased, and the irradiation amount of normal cells can be lessened and the effect of irradiation with a particle beam on the normal cells can be minimized.

The electromagnet, generating a magnetic field through which the particle beam acceleration orbit plane passes, of the cyclotron 20 is made of superconducting coils, as shown in FIG. 28. A plurality of superconducting coils 41 are placed symmetrically with respect to the center in a given space; they are formed at the center with a hollow filled with liquid helium 43 and are accommodated in a liquid helium tank 42 to be maintained at extremely low temperatures. A heat shield 44 is placed so as to surround the helium tank 42 and a vacuum tank 45 surrounds the outer periphery of the heat shield and is maintained under vacuum. A room-temperature pore is at the center of the vacuum tank 45 and a high-frequency acceleration hollow (dee), etc., is placed in a center 48. The outer periphery is surrounded by a magnetic body 46 for shielding a magnetic flux leaked from the outer periphery.

The superconducting coils 41 are maintained at extremely low temperatures by means of the liquid helium 43. For the heat entry from the outside, heat conduction is cut off in a vacuum state in the vacuum vessel 45 and radiation heat is cut off by the heat shield 44. The superconducting coils filled with liquid helium need to be replenished with as much liquid helium as consumed, resulting in a complicated structure.

As described above, in the conventional rotary particle beam irradiation apparatus, the particle orbit plane of the cyclotron is placed at right angles to the radiation shield fixed to the rotation support frame. Thus, the magnetic field distribution in the cyclotron becomes uneven because of the magnetic body used for the radiation shield, whereby the travel direction of a beam in the cyclotron deviates, increasing the amount of the beam coming into collision with the surrounding walls and decreasing the amount of the beam that can be taken out. A radiation generated by the beam coming into collision and a radiation generated by a part of the beam coming into collision with the deflector when the beam is taken out have the strongest distribution in the irradiation chamber direction and enter the irradiation chamber. To avoid the effect of the radiations on the irradiation chamber, the radiation shield needs to be made thicker. If it is made thicker, it becomes heavier and the system also becomes heavier. It is necessary to raise the strength of the building where the system is installed; it is also difficult to assemble the system and the manufacturing costs of the system are increased.

SUMMARY OF THE INVENTION

It is therefore an object of the invention to prevent the internal magnetic field of a cyclotron from being affected by its surrounding magnetic bodies in order to lessen a beam loss in the cyclotron and decrease the amount of radiations into an irradiation room, thus lightening shields for shielding radiations and external magnetic fields, thereby providing a light system.

According to the invention, there is provided a particle beam irradiation apparatus comprising: particle beam circular acceleration means for generating a particle beam such as a proton beam, circularly accelerating the generated particle beam, and emitting a resultant particle beam; beam transport means for transporting the particle beam; irradiation field formation means for irradiating an irradiated body with the particle beam; and rotation means for rotating the particle beam circular acceleration means, the beam transport means, and the irradiation field formation means in one piece, wherein the acceleration orbit plane, i.e. the plane containing the circular paths along which the particles are accelerated, of the particle beam circular acceleration means is placed at right angles to a rotation shaft of the rotation means.

In the particle beam irradiation apparatus of the invention, the particle beam circular acceleration means and the rotation means are placed so that the axis of the particle beam circular acceleration means and the center line of the rotation means become coaxial.

In the particle beam irradiation apparatus of the invention, an extension in an emission direction of the irradiation field formation means is placed so as to cross an extension to the rotation shaft of the rotation means for rotating the particle beam circular acceleration means, the beam transport means, and the irradiation field formation means.

In the particle beam irradiation apparatus of the invention, a rotation frame for supporting the particle beam circular acceleration means, the beam transport means for transporting a particle beam, and the irradiation field formation means for irradiating an irradiated body with the particle beam is disposed at three places of both end faces: the particle beam circular acceleration means and a portion of the irradiation field formation means.

In the particle beam irradiation apparatus of the invention, a radiation shield is placed between the particle beam circular acceleration means and an irradiation room.

In the particle beam irradiation apparatus of the invention, the rotation shield placed between the particle beam circular acceleration means and the irradiation room is placed axially symmetrically with respect to the axis of the particle beam circular acceleration means.

In the particle beam irradiation apparatus of the invention, the radiation shield placed between the particle beam circular acceleration means and the irradiation room is a composite shield comprising a nonmagnetic material and a magnetic material laminated on each other with the nonmagnetic material placed on the side of the particle beam circular acceleration means and the magnetic material on the side of the irradiation room.

In the particle beam irradiation apparatus of the invention, the shield placed between the particle beam circular acceleration means and the irradiation room is a composite shield comprising a radiation shield and a magnetic material laminated on each other with the radiation shield placed on the side of the particle beam circular acceleration means and the magnetic material on the side of the irradiation room and a portion of the radiation shield larger than the outer diameter of the particle beam circular acceleration means is thinned.

In the particle beam irradiation apparatus of the invention, a composite shield comprising a magnetic material and a radiation shield laminated on each other is placed on both side faces of the irradiation room side of the particle beam circular acceleration means and the opposite side thereto with the magnetic material placed on the side of the particle beam circular acceleration means.

In the particle beam irradiation apparatus of the invention, a composite shield comprising a magnetic material and a radiation shield laminated on each other is placed on both side faces of the irradiation room side of the particle beam circular acceleration means and the opposite side thereto and thickness between a portion exceeding the diameter of the particle beam circular acceleration means and the outer periphery is thinned.

In the particle beam irradiation apparatus of the invention, the shield placed on both side faces of the irradiation room side of the particle beam circular acceleration means and the opposite side thereto is a composite laminated shield comprising a radiation shield sandwiched between two magnetic material layers.

In the particle beam irradiation apparatus of the invention, the shield placed on both side faces of the irradiation room side of the particle beam circular acceleration means and the opposite side thereto is a composite shield comprising a magnetic material and radiation shields different in material laminated on each other with the magnetic material placed so as to face the side of the particle beam circular acceleration means.

In the particle beam irradiation apparatus of the invention, the particle beam circular acceleration means has magnetic field generation means formed of superconducting coils, the superconducting coils being filled with no liquefied refrigerant and cooled only by a very-low-temperature refrigerator.

In the particle beam irradiation apparatus of the invention, the center axis of cylinders of the very-low-temperature refrigerator for cooling the superconducting coils is placed in parallel with the rotation shaft of the particle beam circular acceleration means or at least with a very-low-temperature part placed on the bottom.

In the particle beam irradiation apparatus of the invention, the magnetic field generation means of the particle beam circular acceleration means comprises a superconducting coil for generating a main magnetic field and a shielding coil being placed on the outer periphery of the superconducting coil for canceling a magnetic field leaked on the outer periphery of the superconducting coil.

In the particle beam irradiation apparatus of the invention, the magnetic field generation means of the particle beam circular acceleration means comprises a superconducting coil for generating a main magnetic field, a shielding coil being placed on the outer periphery of the superconducting coil for canceling a magnetic field leaked on the outer periphery of the superconducting coil, and a magnetic body placed on the outer periphery of the shielding coil.

In the particle beam irradiation apparatus of the invention, the superconducting coil is formed of a superconducting coil.

In the particle beam irradiation apparatus of the invention, an extension in the direction opposite to the travel direction of a particle beam taken out from the particle beam circular acceleration means crosses the rotation shaft of the rotation means.

In the particle beam irradiation apparatus of the invention, the particle beam circular acceleration means comprises magnetic field generation means and high-frequency voltage application means for circularly accelerating the particle beam, an emission mechanism for taking out the accelerated particle beam, a beam focusing magnet for focusing the particle beam, and a dispersion function correction magnet, wherein the dispersion function at the exit of the particle beam and the value resulting from differentiating the dispersion function on beam travel direction coordinates become almost zero.

According to the invention, there is provided a particle beam irradiation apparatus comprising rotary particle beam irradiation means comprising particle beam circular acceleration means, beam transport means, irradiation field formation means, and means for rotating the particle beam circular acceleration means, the beam transport means, and the irradiation field formation means in one piece, and a plurality of fixed irradiation rooms comprising fixed beam transport means that can be connected to the beam transport means of the rotary particle beam irradiation means and fixed irradiation field formation means for forming the particle beam to any desired shape and irradiating an irradiated body with the particle beam.

In the particle beam irradiation apparatus of the invention, the particle beam circular acceleration means is a cyclotron or synchrocyclotron.

DETAILED DESCRIPTION OF THE PREFERRED EMBODIMENTS

Referring now to the accompanying drawings, there are shown preferred embodiments of the invention.

Embodiment 1

Figure 1:
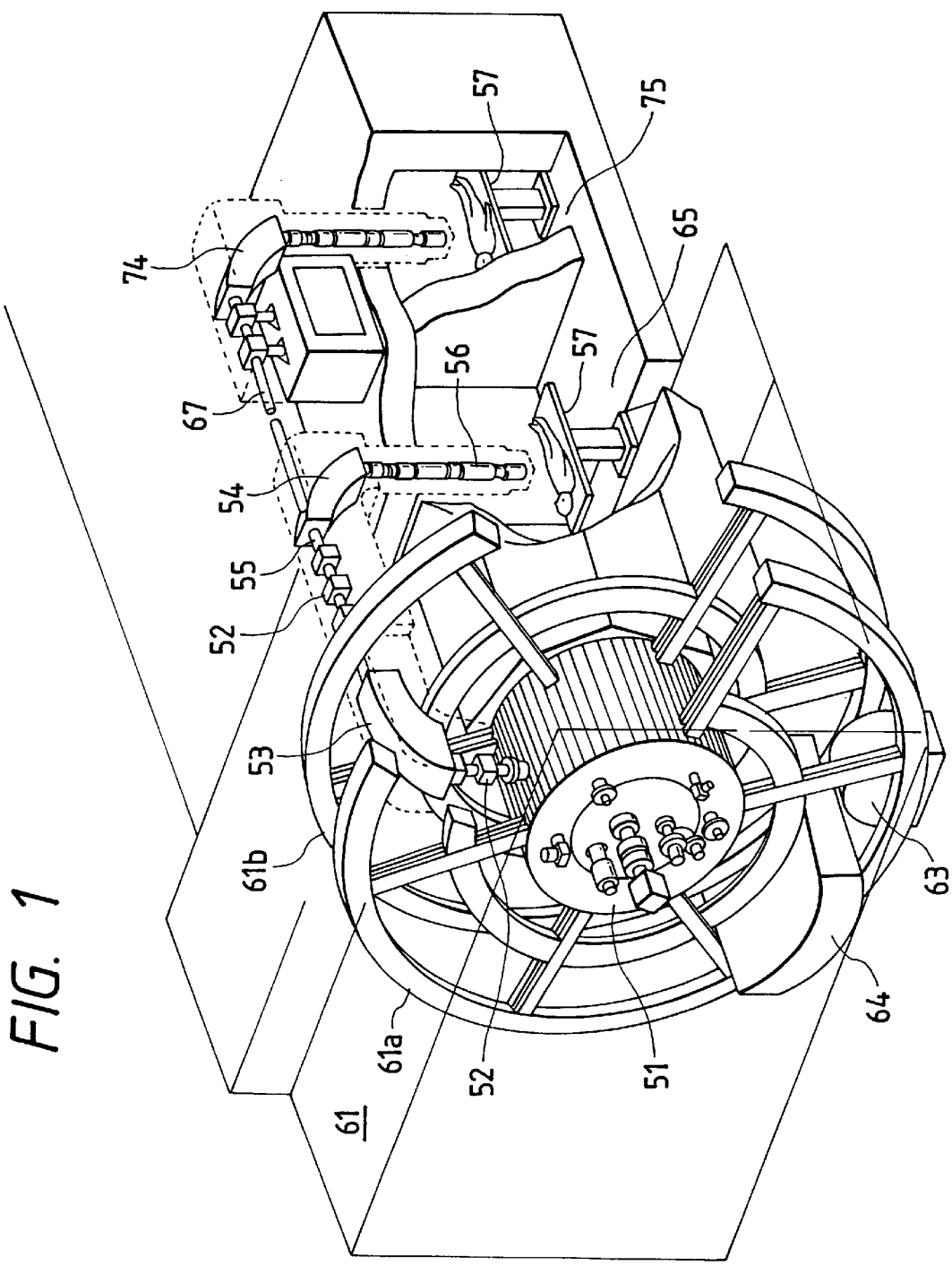
FIG. 1 is a perspective view of a particle beam irradiation apparatus of the invention, shown partly in section.
Figure 2:
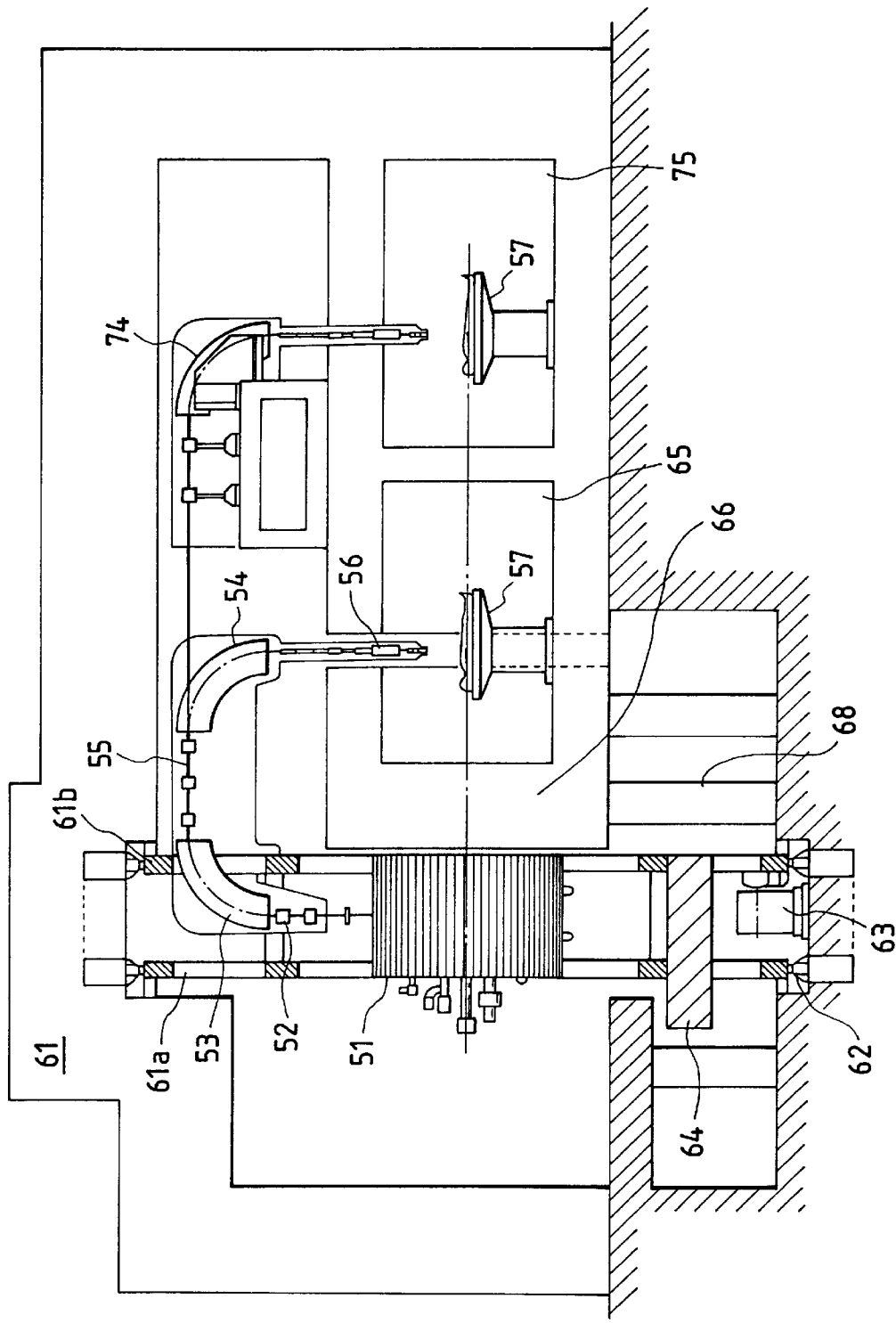
FIG. 2 is a sectional side view of FIG. 1.
Figure 3:
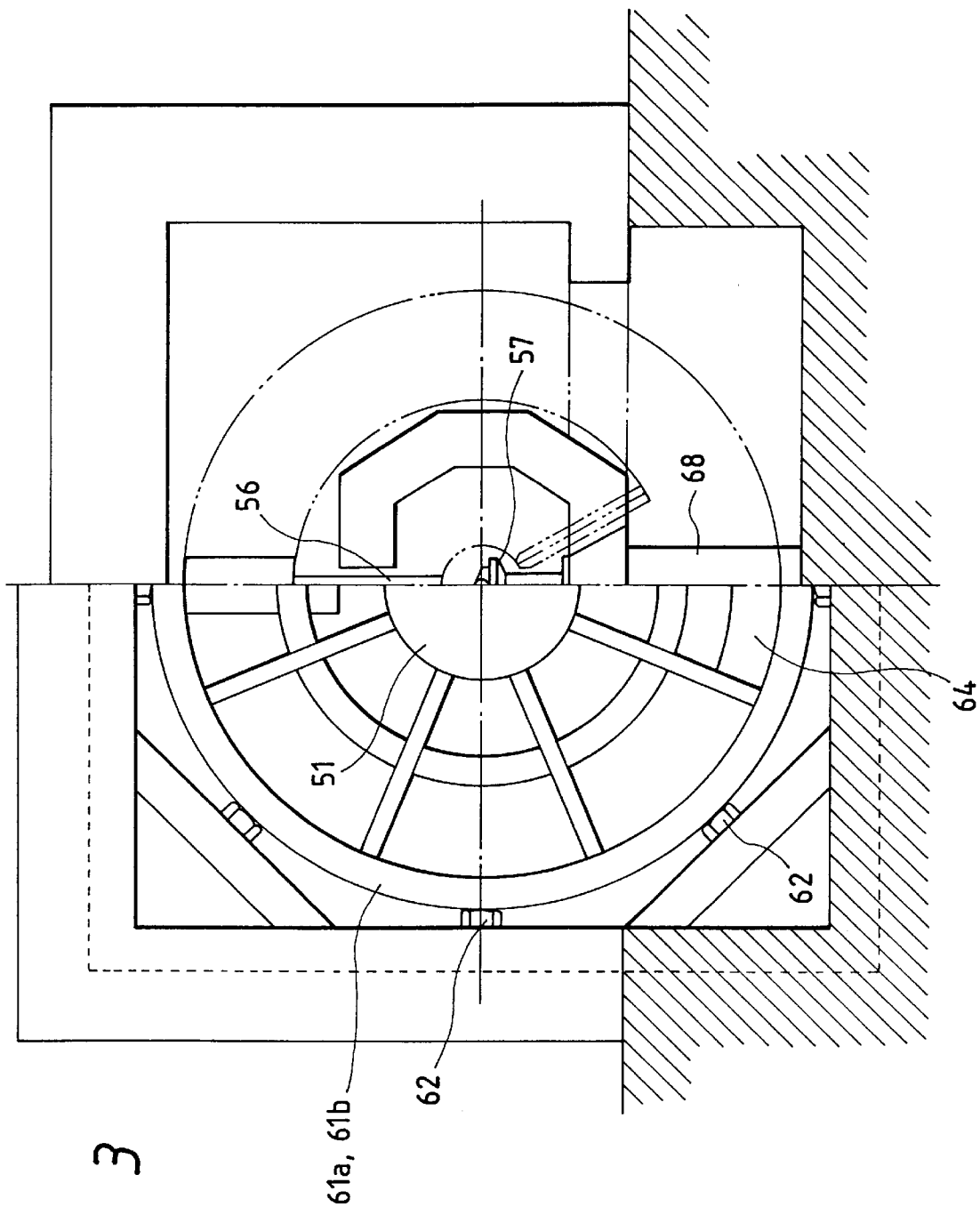
FIG. 3 is a sectional view of a rotation frame portion in FIG. 1.

FIG. 1 is a perspective view of a first embodiment of the invention. FIG. 2 is a longitudinal sectional view of the center in FIG. 1. FIG. 3 is a transverse sectional view of the intermediate part in FIG. 1. In the figures, numeral 51 is a cyclotron of particle beam circular acceleration means for generating a particle beam such as a proton beam, generating a magnetic field, circularly accelerating the particle beam, and emitting a particle beam, numeral 52 is a quadrupole electromagnet for focusing a particle beam, numeral 53 is a deflection electromagnet for deflecting the orbital path of the particle beam emitted from the cyclotron, numeral 54 is a diverting electromagnet for diverting the travel direction of a particle beam, numeral 55 is a beam transport chamber for transporting a particle beam, numeral 56 is an irradiation field formation unit, numeral 57 is a treatment bed on which a human body receiving medical treatment is placed, numeral 61 is a rotation frame to which the cyclotron 51, the quadrupole electromagnet 52, the deflection electromagnet 53, the diverting electromagnet 54, the irradiation field formation unit 56, and any other components are attached for rotating these components in one piece, numeral 62 is a roller for rotatably supporting the rotation frame 61, numeral 63 is a rotation drive for driving the rotation frame 61, and numeral 64 is a balancer for balancing the weight in a state in which the components are attached to the rotation frame 61. Numeral 65 is a rotary treatment room rotating for applying a particle beam to an irradiated body, numeral 66 is a shielding enclosure being placed between the cyclotron 51 and the rotary treatment room 65 for shielding radiations, numeral 67 is a transport chamber for transporting a particle beam, numeral 68 is a pole for supporting the shielding enclosure 66, numeral 74 is a diverting electromagnet on the fixed irradiation room side, and numeral 75 is a fixed treatment room.

In the configuration, the cyclotron 51 of the particle beam circular acceleration means is supported so that the acceleration orbit plane of a particle beam is placed in a direction at right angles to the center axis of the rotation frame 61, and a particle beam is emitted from the outer periphery of the cyclotron 51 toward the direction at right angles to the center axis (upward in the figure). The particle beam emitted from the cyclotron 51 is focused by means of the quadrupole electromagnet 52 and the transport direction of the focused particle beam is changed by means of the deflection electromagnet 53. The particle beam is transported in the beam transport chamber 55, is diverted by means of the diverting electromagnet 54 above the rotary treatment room 65, and enters the irradiation field formation unit 56 for irradiating the target of cancer cells of a cancer patient placed on the treatment bed 57 with the particle beam. The cyclotron 51, the quadrupole electromagnet 52, the deflection electromagnet 53, the diverting electromagnet 54, and the irradiation field formation unit 56 are attached to the rotation frame 61, which is rotated by the rotation drive 63. The extension to the irradiation direction of the irradiation field formation unit 56 is made to cross the center line of the rotation shaft, whereby the cancer cells of the cancer patient can be irradiated with the particle beam from any desired direction.

When the cyclotron 51 is run, it radiates high-speed neutrons. Thus, the radiation shielding enclosure 66 is placed between the cyclotron 51 and the rotary treatment room 65 for preventing the high-speed neutrons from entering the rotary treatment room 65. The rotary treatment room 65 is formed with a notch so that the irradiation field formation unit 56 can rotate. Thus, the portion of the shielding enclosure 66 on the cyclotron 51 side of the rotary treatment room 65 is supported on the pole 68. Therefore, the rotation angle range of the irradiation field formation unit 56 has a blind spot below the treatment bed and about 300 degrees above and left and right of the treatment bed, as shown in FIG. 3.

The treatment bed 57 enables the patient position to be adjusted in three dimensions of back and forth, left and right, and top and bottom so that the cancer cells of the patient can be irradiated with the particle beam.

When a cancer patient is irradiated with a particle beam, considerable time is required for various preparations before the patient is placed on the treatment bed 57. Meanwhile, the particle beam irradiation apparatus stands by. On the other hand, some of patients requiring irradiation with a particle beam may need momentary irradiation while some require a large amount of irradiation. For momentary irradiation, the patient may be irradiated from one direction without trouble and the attachment direction need not be changed for irradiation. The patient may be irradiated from an arbitrary direction depending on the position of the patient. Considering such circumstances, patients who will undergo a small amount of irradiation can be irradiated in the fixed treatment room 75 during the preparations in the rotary treatment room 65, whereby the availability of the particle beam irradiation apparatus can be raised. For irradiation with a particle beam in the fixed treatment room 75, the diverting electromagnet 54 above the rotary treatment room 65 is detached from the end of the beam transport chamber 55 and the end of a beam transport chamber 67 to the fixed treatment room 75 is placed opposite the beam transport chamber 55, whereby the particle beam is introduced into the fixed treatment room 75. In doing so, the availability of the particle beam irradiation apparatus can be raised.

As we have discussed, the orbit plane of a particle beam of the cyclotron 51 of the particle beam circular acceleration means is placed in the direction at right angles to the rotation shaft of the rotation frame 61, whereby the irradiation room can evade the direction in which the radiation produced by a beam coming in collision with the wall or deflector in the cyclotron is the strongest (the same direction as the beam orbit plane). Further, the components of the rotation frame 61 are placed symmetrically with respect to the center axis of the cyclotron 51 and the axial symmetry of the magnetic field distribution of the cyclotron 51 is not disturbed by the components of the rotation frame 61; the beams loss during acceleration can be decreased. Resultantly, the radiations of high-speed neutrons, etc., reduced due to the beam loss can be produced.

The portion for generating a particle beam and irradiating with the particle beam is rotated, whereby the irradiation route of cancer cells of a cancer patient becomes an arbitrary direction, thus the effect of the particle beam on normal cells on the irradiation route can be minimized.

To irradiate with a particle beam, first the particle beam irradiation apparatus is run and an irradiated body is placed on the rotation shaft of the rotation frame 61 on which the particle beam irradiation apparatus is installed, and is irradiated with the particle beam from any desired angle for several minutes. After this, the rotation frame 61 is restored to the former position and a beam is transported to the fixed treatment room 75, then an irradiated body placed in the fixed treatment room 75 is irradiated with the beam for several minutes. Meanwhile, irradiation preparations for another irradiated body are made in the rotary treatment room 65. Upon completion of irradiation in the fixed treatment room 75, the rotation frame 61 is adjusted in rotation so as to set the irradiation angle required for the irradiated body in the rotary treatment room 65, and the irradiated body is irradiated with the beam for several minutes. These steps are repeated. Under the current circumstances, it takes about 30 minutes to make irradiation preparations for an irradiated body and only two persons would be able to be irradiated in an hour in the rotary treatment room 65. However, the configuration according to the invention enables four persons to be irradiated in an hour, so that the availability of the particle beam irradiation apparatus can be raised.

Embodiment 2

Figure 4:
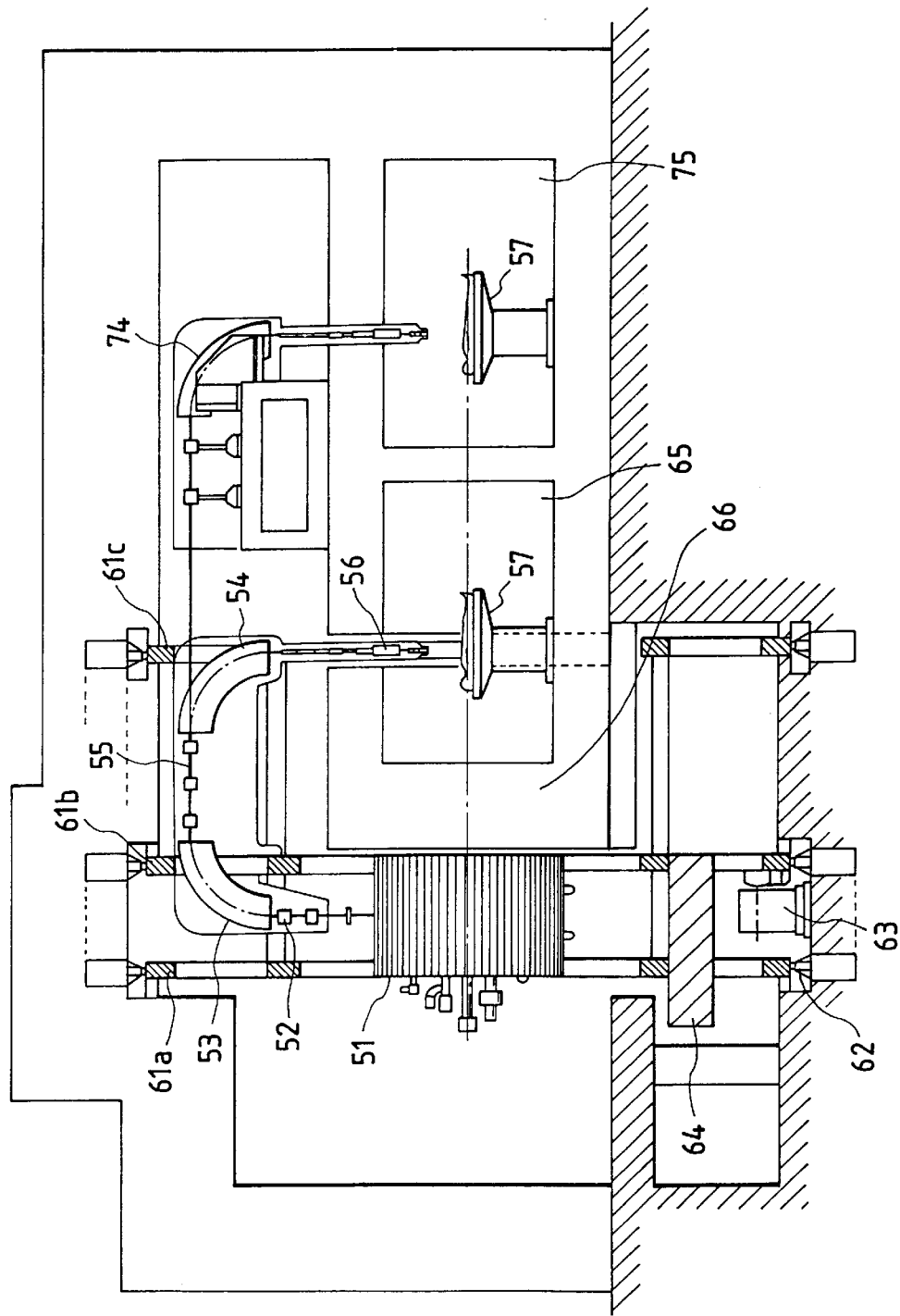
FIG. 4 is a sectional side view of the configuration in FIG. 1 to which another rotation frame is added.

For the rotation frame 61 for rotating the particle beam circular acceleration means, the beam transport means, and the irradiation field formation means in one piece in the configuration of the first embodiment shown in FIGS. 1 and 2, a rotation frame 61c is also disposed in the portion of irradiation field formation means 56 in addition to rotation frames 61a and 61b at both ends of particle beam circular acceleration means 51 in a second embodiment of the invention, as shown in FIG. 4.

The three rotation frames 61a, 61b, and 61c are thus provided, whereby assembly of the portion of the irradiation field formation means 56 is facilitated and the rotation frames 61a, 61b, and 61c are well balanced under load and can be rotated smoothly.

Embodiment 3

Figure 5:
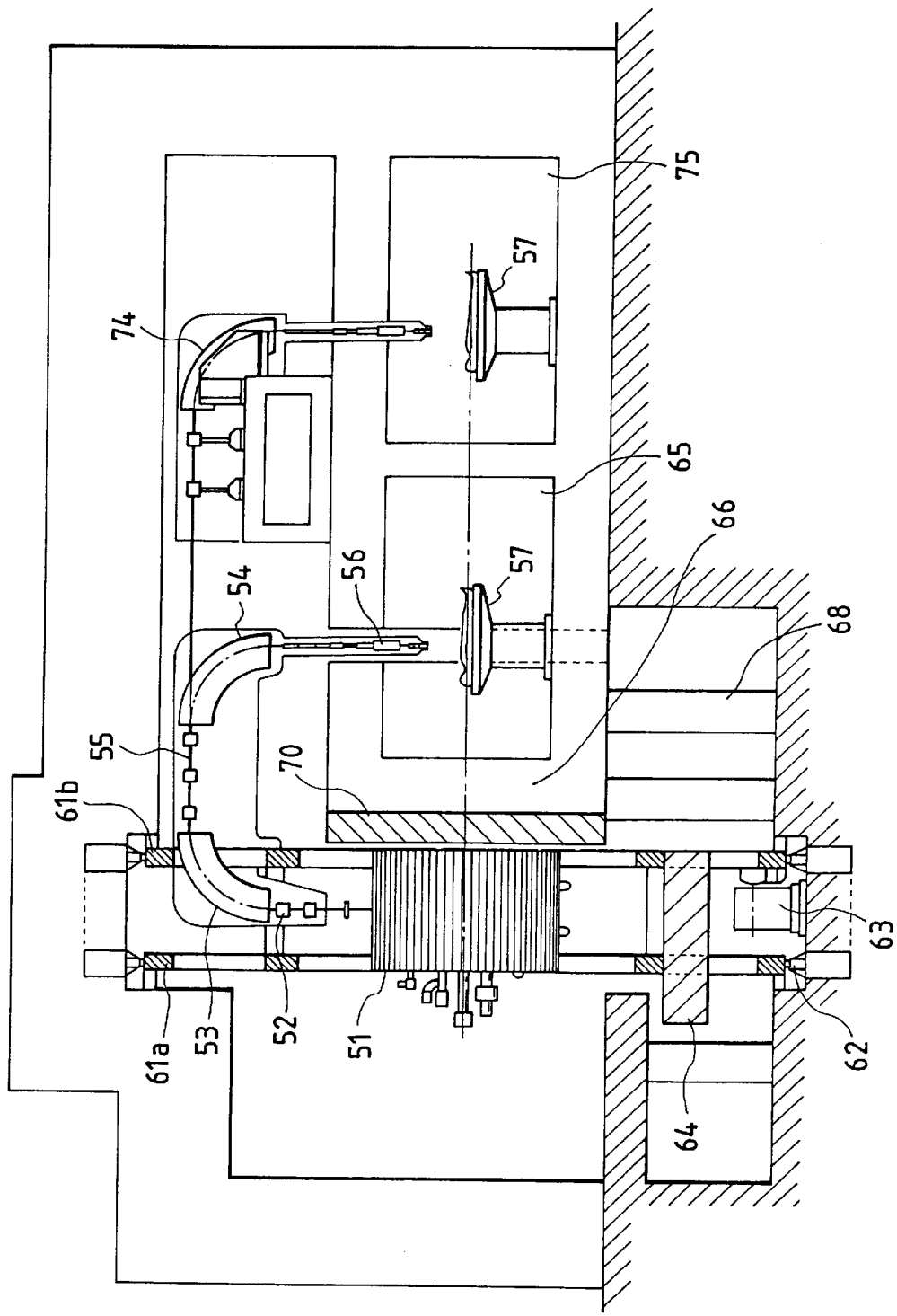
FIG. 5 is a sectional side view of the configuration in FIG. 1 to which a radiation shield is added between particle beam acceleration means and a treatment chamber.

A third embodiment of the invention has the same configuration as the first embodiment except that it comprises a radiation shield 70 for shielding radiations of high-speed neutrons, etc., placed between particle beam circular acceleration means 51 and a rotary irradiation room 65 axially symmetrically with respect to the rotation shaft of rotation means 61, as shown in FIG. 5.

A part of a particle beam accelerated by the particle beam circular acceleration means 51 comes in collision with walls of the circular acceleration means, etc., and is lost. At this time, it emits radiations such as high-speed neutron beams. Since radiations such as high-speed neutron beams adversely affect human bodies, it is indispensable to place a radiation shield between the particle beam circular acceleration means 51 and the treatment room so that the radiations do not enter the treatment room. The radiation shield 70 is placed as shown in FIG. 5, thereby preventing radiations emitted from the particle beam circular acceleration means 51 from entering the rotary treatment room 65 in which an irradiated body is placed, suppressing the adverse effect of the radiations on the irradiated body.

Materials having a large density, such as lead or iron, are used for radiation shields. If iron is used, it is a magnetic substance, so that the uniformity of magnetic fields of the particle beam circular acceleration means 51 is disturbed. If the magnetic fields are disturbed, the amount of particle beams coming in collision with the walls of an acceleration orbit, etc., increases and radiations such as high-speed neutron beams increase. However, the radiation shield 70 is placed axially symmetrically with respect to the axis of the particle beam circular acceleration means 51, whereby the magnetic fields are not disturbed and the leakage amount of radiations such as high-speed neutron beams from the particle beam circular acceleration means 51 can be suppressed.

Embodiment 4

Figure 6:
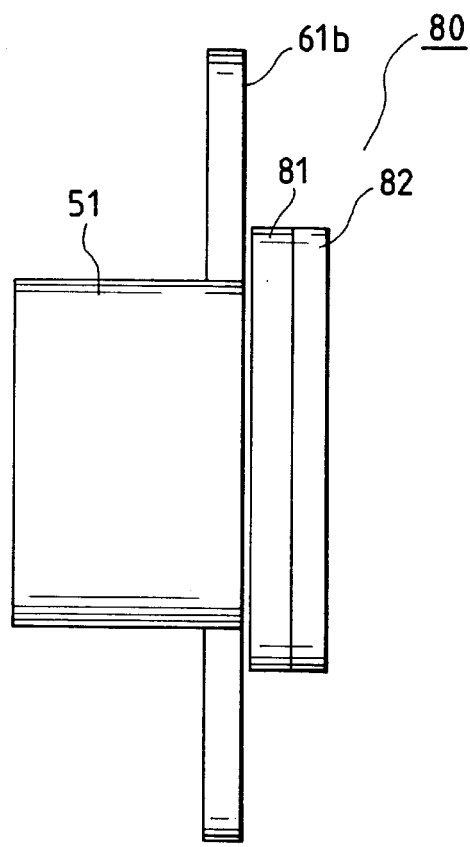
FIG. 6 is a fragmentary drawing to show one structure of the radiation shield in FIG. 5.

In a fourth embodiment of the invention, a composite shield 80 comprising a non-magnetic material and a magnetic material 82 laminated on each other for preventing transmission of radiations is placed on the treatment room 65 side of particle beam circular acceleration means 51 with the non-magnetic material 81 on the side of the particle beam circular acceleration means 51 so that the shape of the non-magnetic material becomes axially symmetric with respect to the shaft of the particle beam circular acceleration means 51, as shown in FIG. 6.

The particle orbit plane of the particle beam circular acceleration means 51 requires a uniform magnetic field and to provide uniformity of magnetic fields, the outer periphery of a coil needs to be shielded by a magnetic material of iron, etc., to eliminate the effect of external magnetic fields. An electromagnetic mechanical force inversely proportional to the distance between the magnetic material and coil acts between the magnetic material and coil. As the magnetic material is made to approach the coil, the electromagnetic mechanical force grows. Thus, the composite shield 80 comprising the nonmagnetic material and the magnetic material 82 laminated on each other has the non-magnetic material 81 placed on the side of the particle beam circular acceleration means 51 and the magnetic material 82 apart from the particle beam circular acceleration means 51, thereby producing the effect of decreasing the electromagnetic mechanical force acting between the composite shield 80 and the coil. The configuration of the fourth embodiment also produces the effect of enhancing the uniformity of magnetic field as with the third embodiment.

Figure 7:
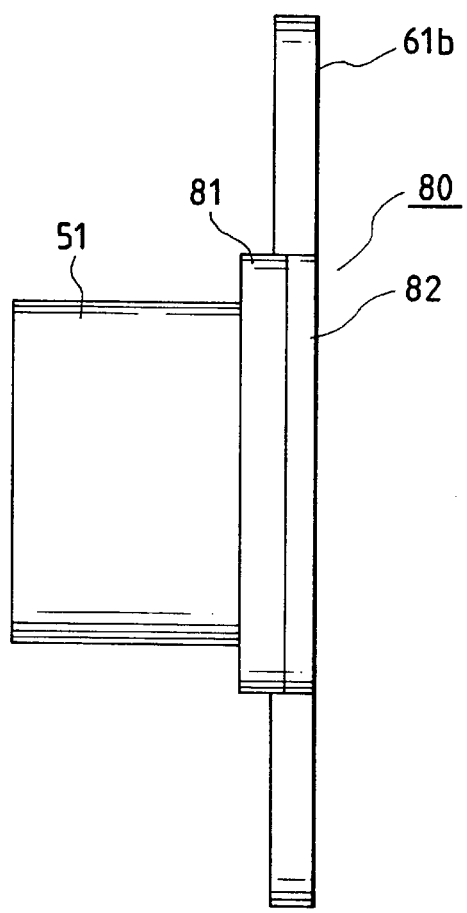
FIG. 7 is a fragmentary drawing to show another structure of the radiation shield in FIG. 5.

If the composite shield 80 is placed in the portion of a rotation frame 61, as shown in FIG. 7, the rotation frame is well balanced under the load of the particle beam circular acceleration means and the rotation part can be rotated more smoothly.

Embodiment 5

Figure 8:
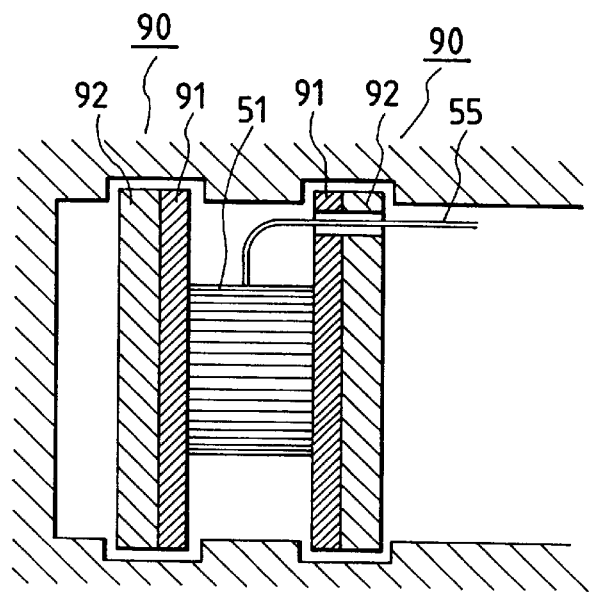
FIG. 8 is a fragmentary drawing to show a state in which a shield is attached to both side faces of particle beam circular acceleration means.

A fifth embodiment of the invention comprises a shield placed on both sides of particle beam circular acceleration means 51, as shown in FIG. 8. In the figure, numeral 90 is a composite shield comprising a magnetic material 91 and a radiation shield 92 laminated on each other. One composite shield 90 is placed on the treatment room 65 side of the particle beam circular acceleration means 51 and the other composite shield 90 is placed on the opposite side with the magnetic material 91 on the particle beam circular acceleration means side.

In the configuration, the electromagnetic mechanical force acting between the particle beam circular acceleration means 51 and the magnetic material 91 is canceled between the magnetic materials 91 on both side faces of the particle beam circular acceleration means 51, so that the particle beam circular acceleration means 51 becomes mechanically stable.

Embodiment 6

Figure 9:
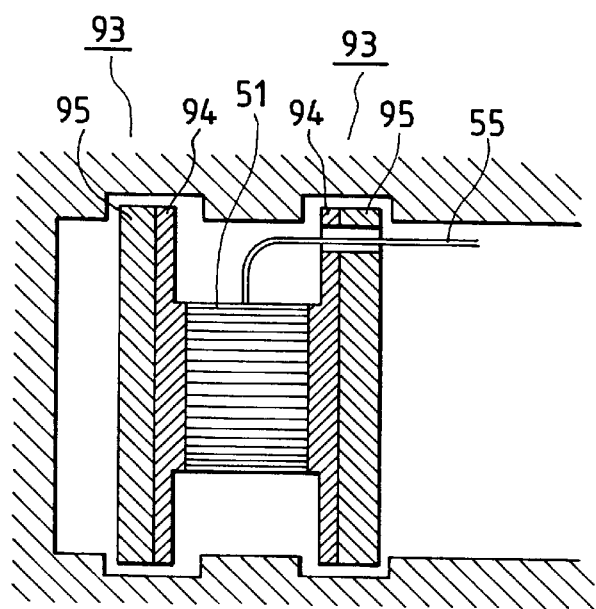
FIG. 9 is a fragmentary drawing where portions of the shield in FIG. 8 larger than the outer periphery of particle beam circular acceleration means 51 are thinned.

In a sixth embodiment of the invention, portions of the composite shield in the fifth embodiment larger than the outer diameter of particle beam circular acceleration means are thinned, as shown in FIG. 9. In the figure, numeral 93 is a composite shield comprising a magnetic material 94 and a radiation shield 95 laminated on each other. The portions of the magnetic material 94 larger than the outer periphery of particle beam circular acceleration means 51 are thinned.

Since the magnetic flux leaked from the outer periphery of the particle beam circular acceleration means 51 lessens, necessary shielding is provided sufficiently even if the magnetic materials 94 are thinned. The magnetic materials 94 are thus thinned, whereby the system becomes light and the drive force of the rotation part can be lessened.

Embodiment 7

Figure 10:
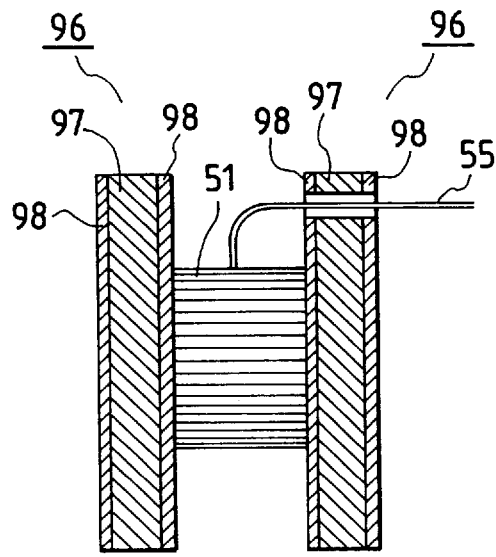
FIG. 10 is a fragmentary drawing to show a state in which another shield is attached to both side faces of particle beam circular acceleration means.

In a seventh embodiment of the invention, a composite shield 96 placed on both sides of particle beam circular acceleration means 51 comprises a radiation shield 97 sandwiched between magnetic materials 98, as shown in FIG. 10.

In the structure, the magnetic materials 98 of each shield 96 are thin and the radiation shields 97 can be placed near the radiation generation source of the particle beam circular acceleration means 51, thus the allowance angle from the radiation generation source becomes large, and the radiation shields 97 can be thinned as compared with shielding at a distant place. Since dual magnetic materials 98 between which the radiation shield 97 is sandwiched are used, the shielding effect of external magnetic fields can be raised as compared with single shielding.

Embodiment 8

Figure 11:
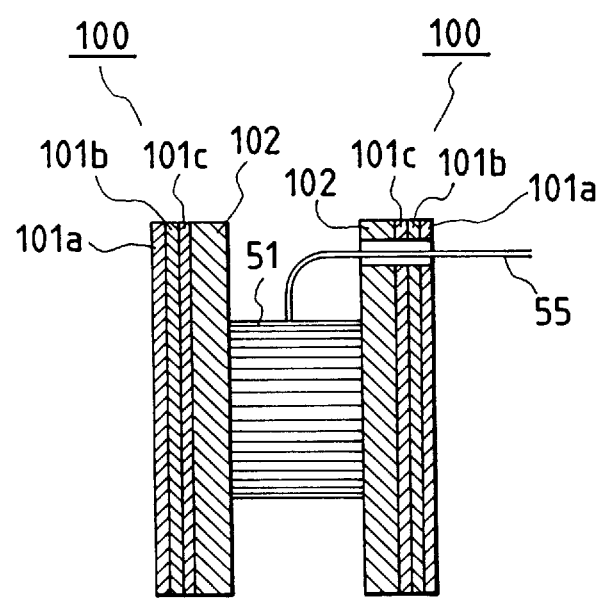
FIG. 11 is a fragmentary drawing to show a state in which another shield is attached to both side faces of particle beam circular acceleration means.

In an eighth embodiment of the invention, a composite shield comprises radiation shields different in material laminated on each other and a magnetic material, the radiation shields and the magnetic material being laminated, as shown in FIG. 11. In the figure, numeral 100 is a composite shield placed on both sides of particle beam circular acceleration means 51, numeral 101 is a magnetic material, and numerals 102*a*, 102*b*, and 102*c* are radiation shields different in material laminated on each other.

A radiation emitted from the particle beam circular acceleration means 51 contains several types of particles different in characteristic and to use a single shield material for shielding, the shield material needs to be thickened considerably. The energy distribution of radiations emitted from the particle beam circular acceleration means 51 is grasped and materials having the shielding effect are selected in response to the radiation types and are laminated, whereby the composite shield 100 can be thinned, so that the weight of the system can be reduced.

Embodiment 9

Figure 23:
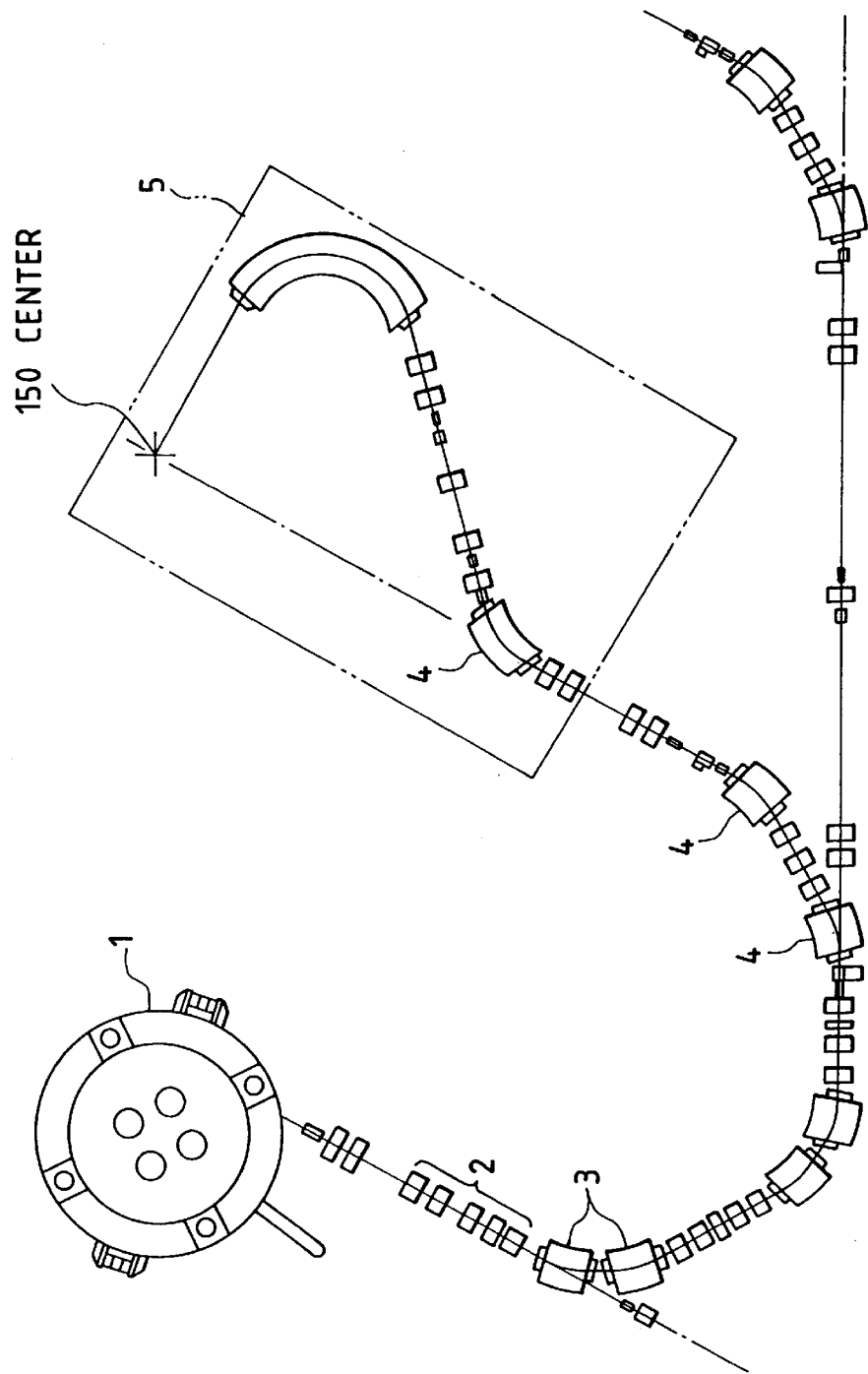
FIG. 23 is a drawing to show the configuration of a conventional particle beam irradiation apparatus.
Figure 25:
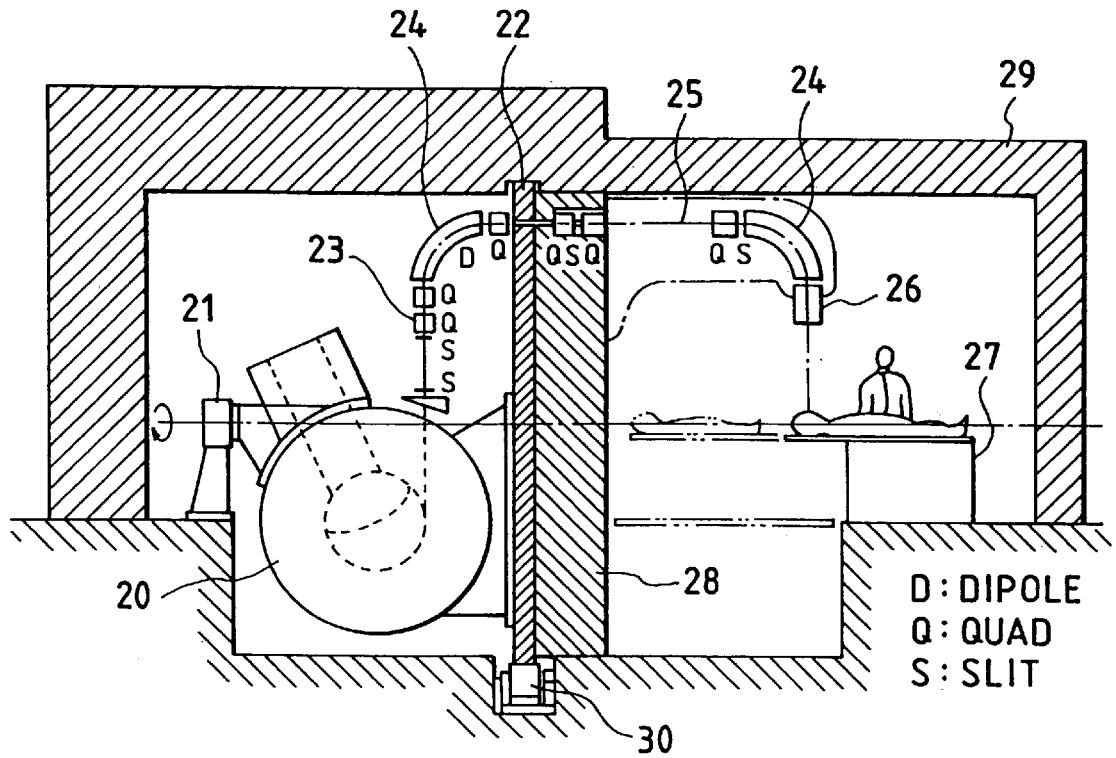
FIG. 25 is a drawing to show the configuration of another conventional particle beam irradiation apparatus.
Figure 26:
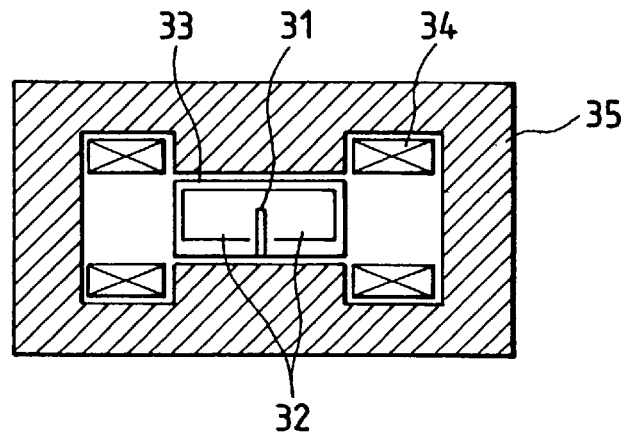
FIG. 26 is a sectional view to schematically show conventional particle beam acceleration means.
Figure 27:
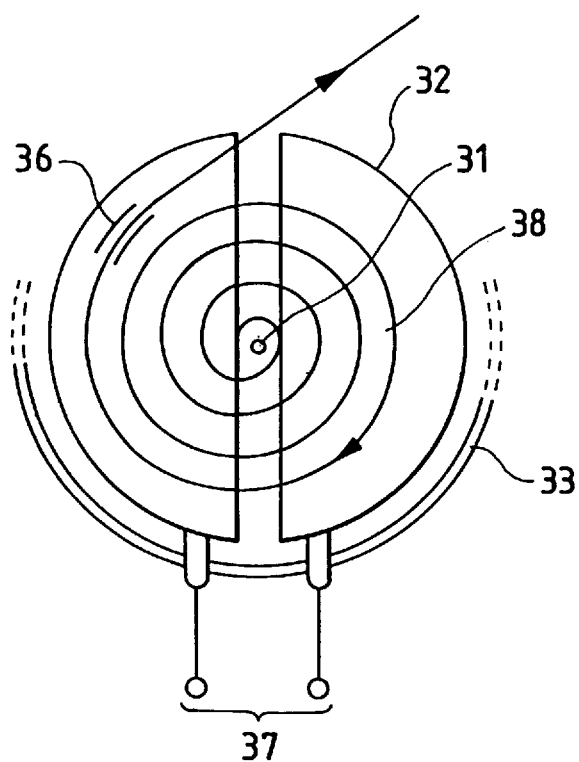
FIG. 27 is an illustration to explain the operation of the conventional particle beam acceleration means.
Figure 28:
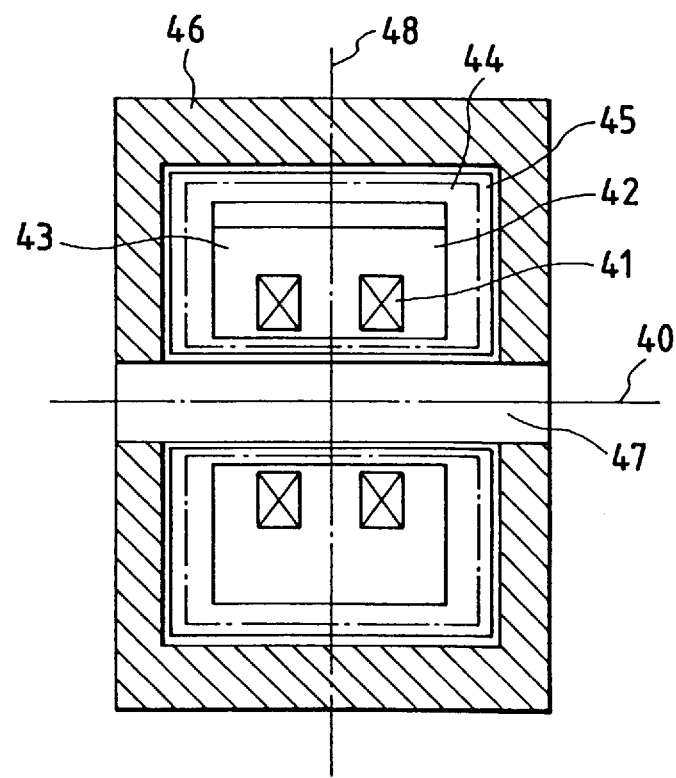
FIG. 28 is a fragmentary drawing where excitation coils of the conventional particle beam acceleration means are made of superconducting coils.

A ninth embodiment of the invention uses superconducting coils as excitation coils for generating a magnetic field on the acceleration orbit of particle beam circular acceleration means and cools and maintains the superconducting coils at very low temperatures without using liquid helium. For superconducting electromagnets of the conventional concept, as shown in FIG. 23, the superconducting coils 41 are immersed in the liquid helium 43 and are maintained at very low temperatures. However, a refrigerator using adiabatic expansion to generate very low temperatures goes into actual use and can be used to maintain very low temperatures without using liquid helium.

Figure 12:
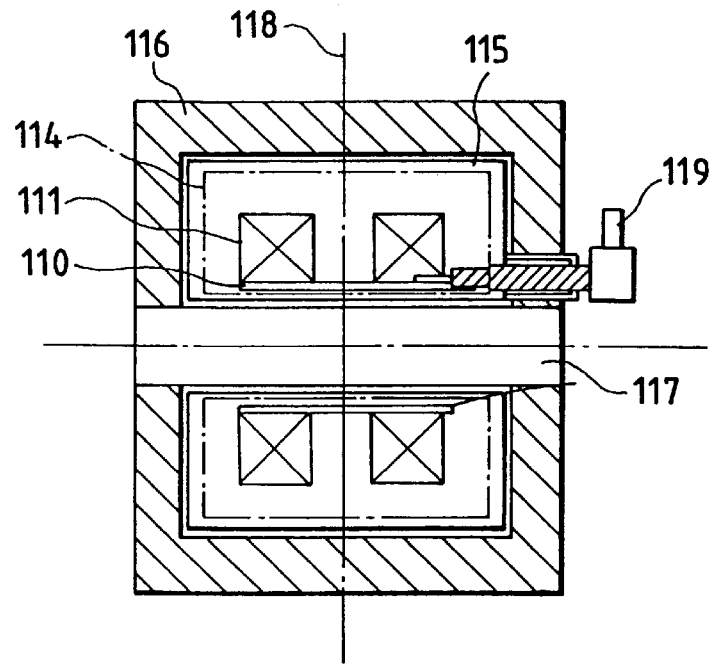
FIG. 12 is a fragmentary drawing of a configuration wherein superconducting coils are used as excitation coils of particle beam circular acceleration means and only a refrigerator is used for cooling.

FIG. 12 shows the configuration of the ninth embodiment. In the figure, numeral 110 is a heat exchanger plate and numeral 111 is a superconducting coil for generating a uniform magnetic field at the center of a center 118 of a room-temperature pore 117 at the center. A plurality of the superconducting coils 111 are placed in contact with the heat exchanger plate 110 symmetrically with respect to the center of the center 118. Numeral 114 is a heat shield of one or more layers placed so as to surround the superconducting coils 111 with a predetermined spacing therebetween, numeral 115 is a vacuum tank for accommodating the superconducting coils 111 surrounded by the heat shield 114, the vacuum tank 115 being maintained under vacuum, and numeral 116 is a magnetic shield for surrounding the outer periphery of the vacuum tank 115, defining a magnetic path of an outer peripheral magnetic field generated by the superconducting coils 111, and shielding the magnetic field leaked to the outside. Numeral 117 denotes a room-temperature pore penetrating the center and numeral 118 denotes the center of the coil unit. Numeral 119 is a very-low-temperature refrigerator using adiabatic expansion to generate very low temperatures with a very-low-temperature part at the tip being thermally connected to the heat exchanger plate 110 and an intermediate temperature part at the intermediate place being thermally connected to the heat shield.

The very-low-temperature refrigerator 119 comprises two or three stages of cylinders, each of which is filled with a heat reservation material appropriate for generated temperatures for compressing and expanding helium gas for generating very low temperatures at the extreme tip. For temperatures at the tip and the intermediate portion, for example, with a 3-stage, very-low-temperature refrigerator, the first stage is cooled to about 80° K., the second stage to about 20° K., and the tip at the third stage to about 4° K. When the tip of the refrigerator 119 is connected to the superconducting coil 111 and the second and third stages are connected thermally to the heat shield 114 for cooling to the intermediate temperatures, the heat entry caused by radiation from the wall faces of the vacuum tank can be prevented. The very-low-temperature refrigerator using adiabatic expansion uses helium gas as internal refrigerant gas for cooling the first stage, the second stage, and the third stage in sequence for generating very low temperatures at the third stage. Whenever the helium gas is cooled, it grows in density and becomes heavy. Thus, if the very-low-temperature part is placed on the top, a convection current where the gas cooled to a low temperature moves to the high-temperature part occurs, lowering the cooling efficiency. To maintain the very low temperatures, it is necessary to place the very-low-temperature part lower than the horizontal position or the axis.

If the superconducting coils 111 are thus shielded thermally and cooled by the very-low-temperature refrigerator 119, they are not accommodated in a liquid helium tank, thus no helium vessel becomes necessary and a part for replenishing liquid helium is also eliminated, so that the particle beam circular acceleration means becomes small-sized and light, leading to small-sized and light rotation means of the particle beam irradiation apparatus to which the invention is applied. It is also unnecessary to replenish electromagnets with liquid helium, and handling also becomes easy.

Embodiment 10

Figure 13:
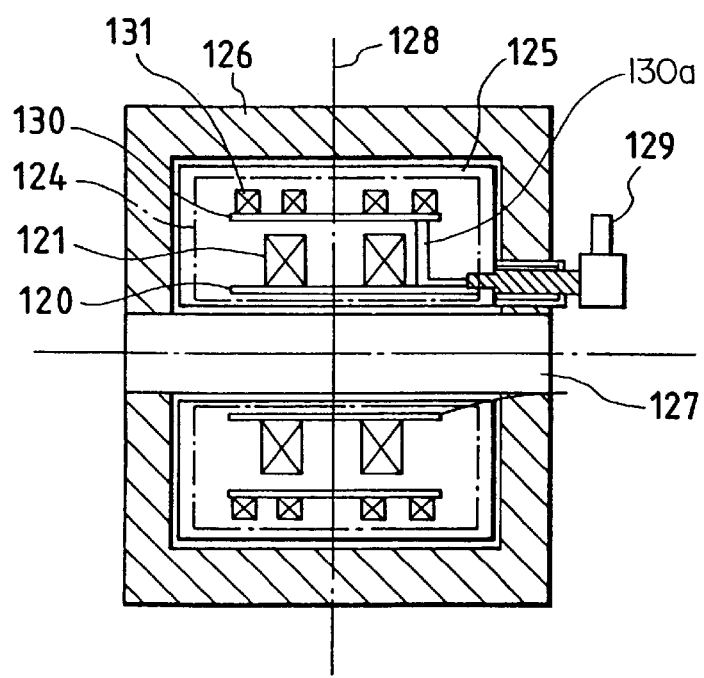
FIG. 13 is a fragmentary drawing of a configuration wherein superconducting coils are used as excitation coils and shielding coils of particle beam circular acceleration means and only a refrigerator is used for cooling.

A tenth embodiment of the invention uses superconducting coils as excitation coils for generating a magnetic field on a particle beam acceleration orbit and has shielding coils for canceling a magnetic field on the outer periphery. FIG. 13 shows the configuration of the embodiment. In the figure, numeral 120 is a main coil heat exchanger plate, numeral 121 is a main superconducting coil for generating a magnetic field on a particle beam acceleration orbit, numeral 124 is a heat shield of one or more layers placed so as to surround the main superconducting coils 121 with a predetermined spacing therebetween, numeral 125 is a vacuum tank for accommodating the main superconducting coils 121 surrounded by the heat shield 124, the vacuum tank 125 being maintained under vacuum, and numeral 126 is a magnetic shield for surrounding the outer periphery of the vacuum tank 125, defining a magnetic path of an outer peripheral magnetic field generated by the main superconducting coils 121, and shielding the magnetic field leaked to the outside. Numeral 127 denotes a room-temperature pore penetrating the center and numeral 128 denotes the center of the coil unit. Numeral 129 is a very-low-temperature refrigerator using adiabatic expansion to generate very low temperatures with a very-low-temperature part at the tip being thermally connected to the heat exchanger plate 120 and the intermediate part being thermally connected to the heat shield 124. Numeral 130 is a shielding coil heat exchanger plate and numeral 131 is a shielding coil for canceling an external magnetic field of the main superconducting coil 121. The shielding coils 131 are connected thermally to the heat exchanger plate 130 and are excited in a direction opposite to the excitation direction of the main superconducting coils 121 so as to cancel the external magnetic fields of the main superconducting coils. Numeral 130a is a thermal conductor for thermally coupling the heat exchanger plate 120 of the main superconducting coils 121 and the heat exchanger plate 130 of the shielding coils 131.

In the configuration, the magnetic fields on the outer peripheries of the main superconducting coils 121 are shielded by the shielding coils 131, so that the outer peripheral magnetic fields are eliminated even if magnetic shields on the outer periphery are little used, leading to light particle beam circular acceleration means. Since the main superconducting coils 121 and the shielding coils 131 are cooled at very low temperatures by the very-low-temperature refrigerator 129, the superconductive state is maintained without using liquid helium and a device for replenishing liquid helium becomes unnecessary as with the ninth embodiment, leading to a simple configuration of the system. An intricate job for replenishing liquid helium also becomes unnecessary and simply configured particle beam circular acceleration means is provided.

Embodiment 11

Figure 14:
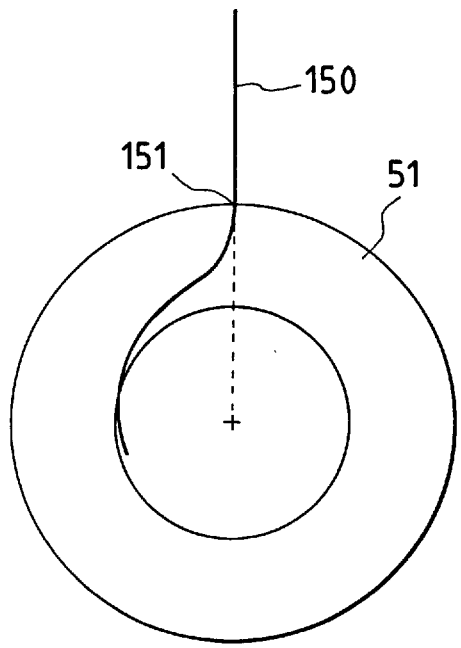
FIG. 14 is an illustration of a particle beam orbit of a particle beam emitted from particle beam circular acceleration means.
Figure 15:
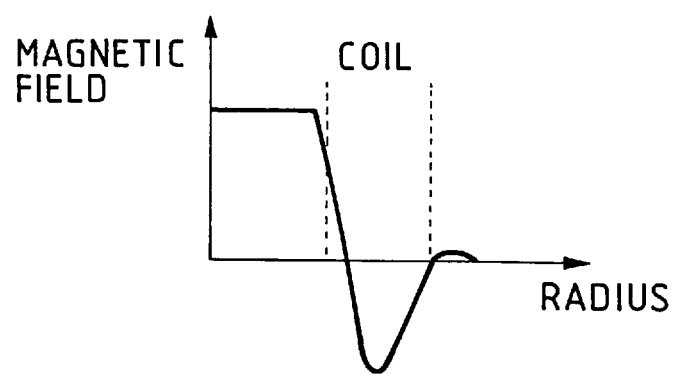
FIG. 15 is a distribution chart of the magnetic field strength in the radial direction of particle beam circular acceleration means.

An eleventh embodiment of the invention is an embodiment of an emitting mechanism of particle beam circular acceleration means 51 of a particle beam irradiation apparatus, such as a cyclotron. FIG. 14 shows an emission orbit of a particle beam accelerated by a cyclotron. In the figure, numeral 51 denotes a cyclotron and numeral 150 denotes a particle beam orbit. FIG. 15 shows a magnetic field distribution in the radial direction of the cyclotron 51. As shown here, the magnetic field in the cyclotron 51 is flat in the central part and in the coil part, the magnetic flux decreases to zero as the magnetic field approaches the outer periphery, and becomes the opposite direction farther into the outer periphery. Therefore, the accelerated particle beam is deflected in the opposite direction on the outer periphery of the coil part.

In the example, the emission angle of a particle beam at a beam outlet 151 depends on the magnetic field strength in the main coils, the magnetic field strength in the cyclotron, and the energy of the particle beam. By adjusting these values, the emission mechanism is adjusted so that the particle beam is emitted in the direction along the extension to the line connecting the emission position and the center of the cyclotron 51.

Figure 16:
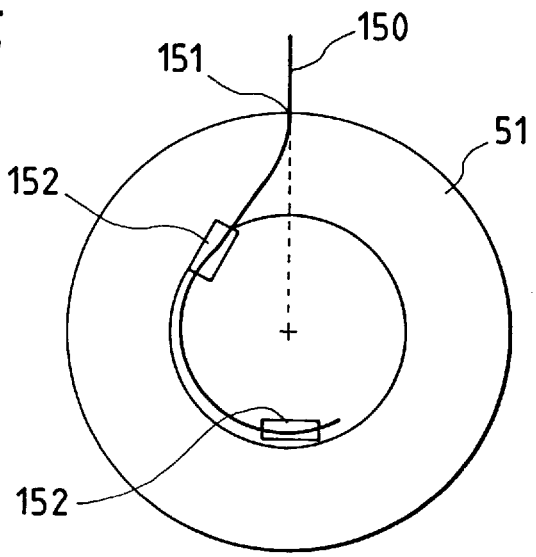
FIG. 16 is an illustration of an adjustment mechanism for adjusting a direction in which a particle beam is emitted from particle beam circular acceleration means.

FIG. 16 shows a configuration wherein a plurality of beam emitting devices 152 for kicking a beam out to the outer periphery are placed in the cyclotron 51. A particle beam kicked by the beam emitting device 152 in the circumferential direction from the orbit of the cyclotron 51 is furthermore kicked in the circumferential direction by the second beam emitting device 152 behind that beam emitting device 152 and is incident on a main coil. The emission angle at the beam outlet 151 is adjusted by adjusting the kick angles of the beam emitting devices 152 considering the incident angle on the main coil, the magnetic field strength in the main coil, etc., so that the particle beam emission direction becomes the direction along the extension to the line connecting the emission position and the center of the cyclotron 51.

Figure 17:
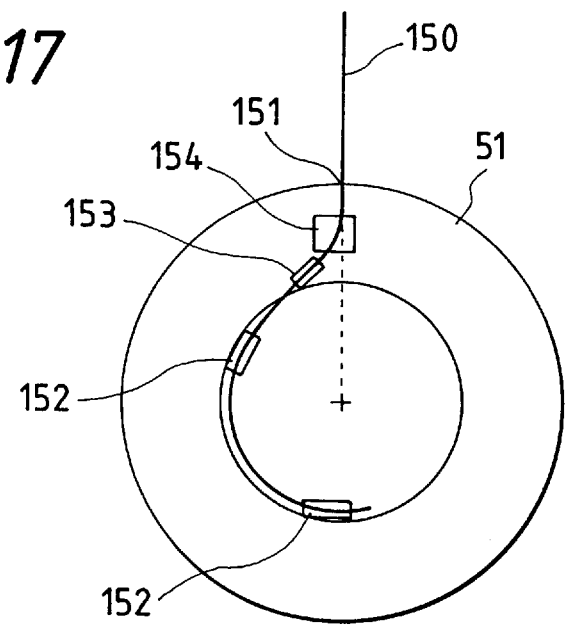
FIG. 17 is an illustration of another adjustment mechanism for adjusting a direction in which a particle beam is emitted from particle beam circular acceleration means.

FIG. 17 shows a configuration wherein a beam deflection angle correction magnet 154 and a beam focusing magnet 153 adjust the emission angle and focus of a particle beam kicked out into the main coil by the beam emitting devices 152 from the beam orbit. The particle beam incident on the inside of the main coil is deflected by an internal magnetic field of the main coil and the beam deflection angle correction magnet 154 placed in the main coil, and a quadrupole magnetic field component occurring in the main coil is corrected by the beam focusing magnet 153. The beam emission angle is adjusted by adjusting the beam deflection angle correction magnet 154 so that the beam emission direction becomes the direction along the extension to the line connecting the emission position and the center of the cyclotron 51.

Figure 18:
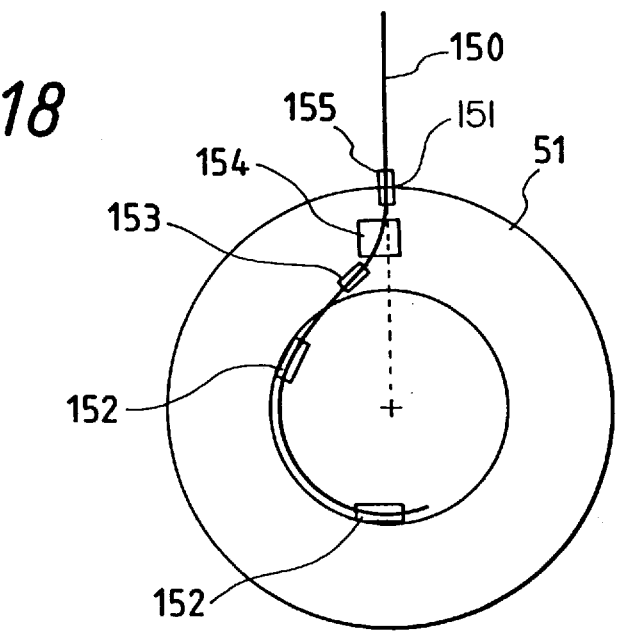
FIG. 18 is an illustration of a further adjustment mechanism for adjusting a direction in which a particle beam is emitted from particle beam circular acceleration means.

FIG. 18 shows a configuration example wherein a beam emission angle correction magnet 155 is placed at the beam outlet 151 in addition to the configuration in FIG. 17. The incident angle of a particle beam on the main coil is adjusted by adjusting the incident angle on the main coil, the magnetic field strength in the main coil, and the kick angle of the second and later beam emitting devices 152 and the beam angle at the beam outlet 151 is finely adjusted by the beam emission angle correction magnet 155 at the beam outlet 151 so that the particle beam emission direction at the beam outlet 151 becomes the direction along the extension to the line connecting the emission position and the center of the cyclotron 51.

This configuration always provides beams of the same quality even if irradiation field formation means rotates around an irradiated body and changes in position.

Embodiment 12

Figure 19:
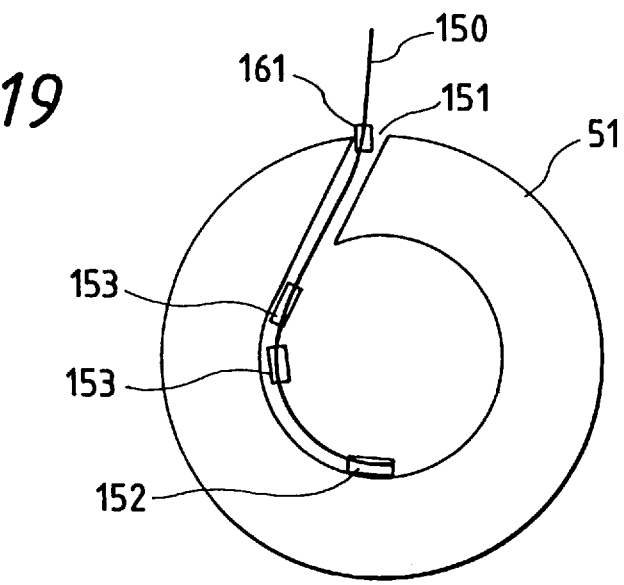
FIG. 19 is an illustration of another adjustment mechanism for adjusting a direction in which a particle beam is emitted from particle beam circular acceleration means.
Figure 20:
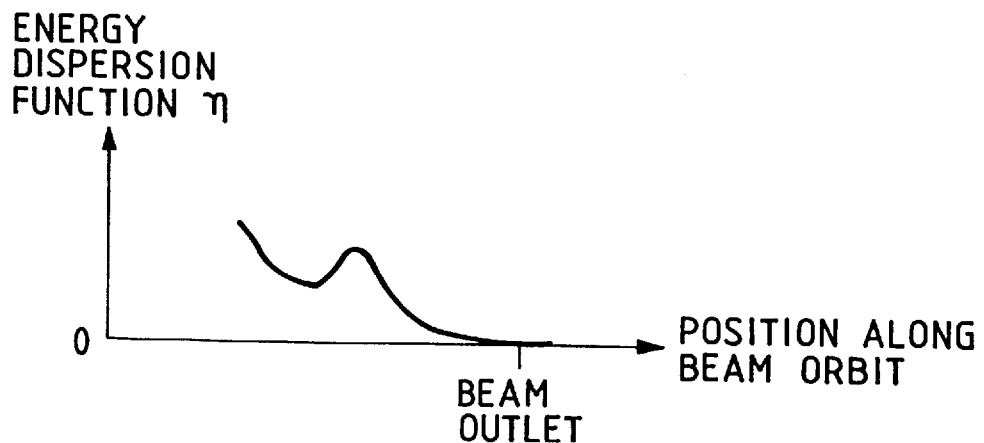
FIG. 20 is a characteristic diagram of an example of a dispersion function of a particle beam emitted from particle beam circular acceleration means.

FIG. 19 shows an example wherein a dispersion function correction magnet 161 is placed at a beam outlet 151 of particle beam circular acceleration means 51 in addition to the configuration of the eleventh embodiment. A particle beam accelerated in the particle beam circular acceleration means 51 is kicked out to the outer periphery by a beam emitting device 152, passes through a magnetic field generated by main coils and beam focusing magnets 153, and arrives at the beam outlet 151. Beam dispersion function $\eta$ changes due to a magnetic field component on the beam orbit, as shown in FIG. 20. The beam dispersion function $\eta$ at the beam outlet 151 is determined by the magnetic field generated by the main coil and the beam focusing magnets 153 in the particle beam circular acceleration means 51. In the example in FIG. 19, adjustments are made by one or more beam focusing magnets 153 and the dispersion function correction magnet 161 placed in the particle beam circular acceleration means 51 so that $\eta$ and the derivative value of $\eta$ at the position of the beam outlet 151 (gradient of beam orbit direction) become zero.

Figure 21:
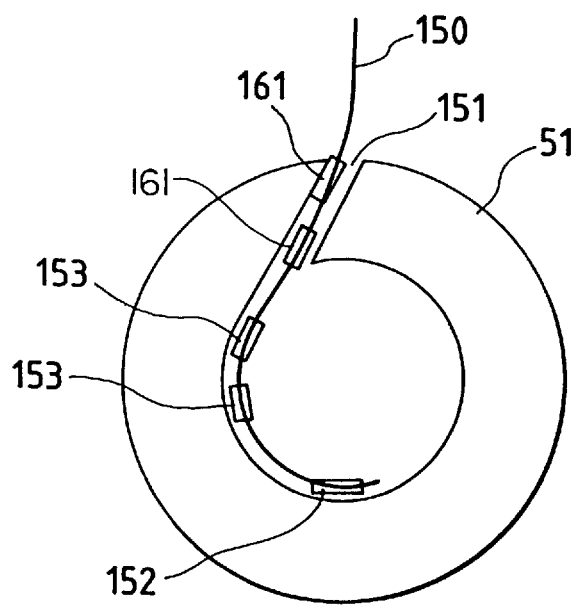
FIG. 21 is an illustration of a further adjustment mechanism for adjusting a direction in which a particle beam is emitted from particle beam circular acceleration means.
Figure 22:
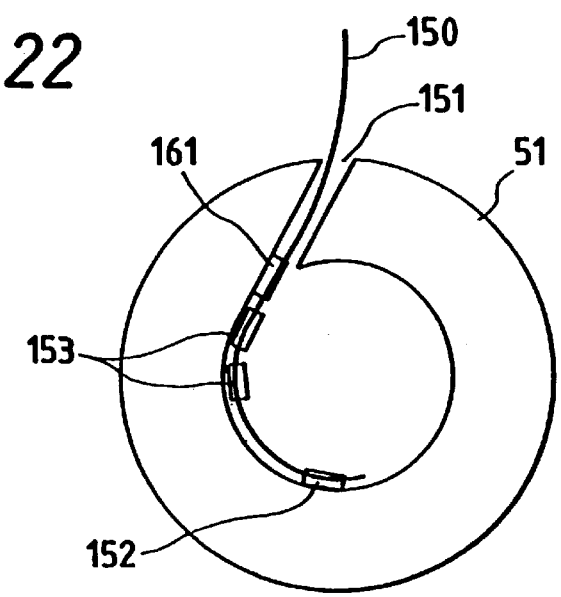
FIG. 22 is an illustration of another adjustment mechanism for adjusting a direction in which a particle beam is emitted from particle beam circular acceleration means.
Figure 24:
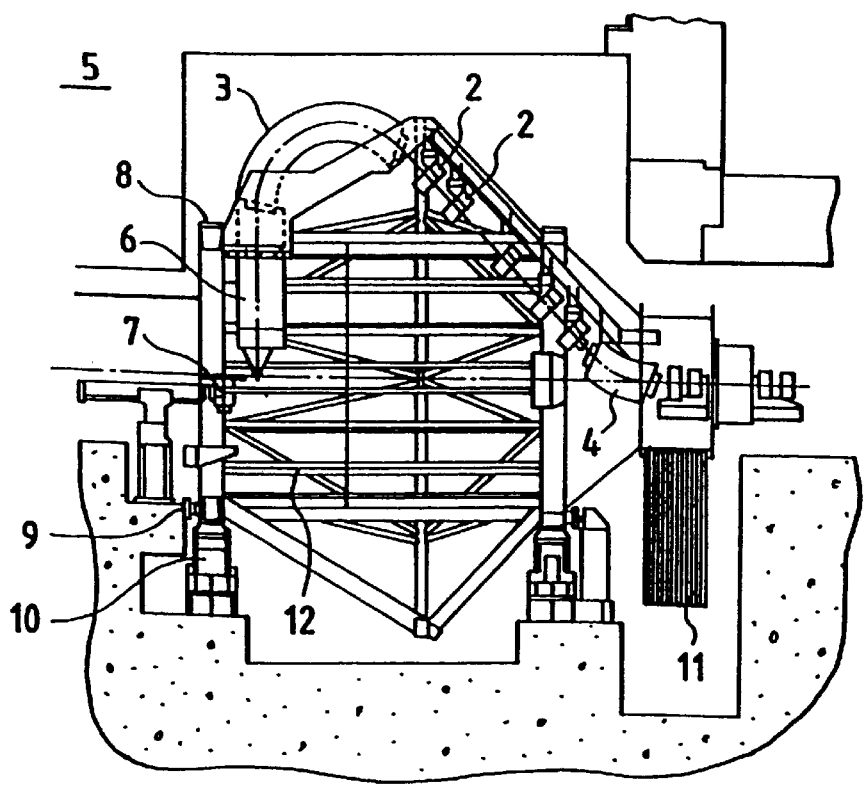
FIG. 24 is a fragmentary drawing to show the configuration of an irradiation part in FIG. 18.

FIG. 21 shows an example where the strength of a magnetic field generated by the main coils of the particle beam circular acceleration means 51 is weak. A plurality of dispersion function correction magnets 161 are placed in the main coils for adjustments so that $\eta$ and the derivative value of $\eta$ (gradient of beam orbit direction) at the position of the beam outlet 151 become zero. FIG. 22 shows an example wherein dispersion function correction magnet 161 and beam focusing magnet are placed in the main coils for adjustments so that $\eta$ and the derivative value of $\eta$ at the position of the beam outlet 151 become zero.

This configuration eliminates the need for a magnet for no dispersion in the beam transport channel after exiting the particle beam circular acceleration means 51, and can provide a compact system.

The particle beam irradiation apparatus comprises particle beam circular acceleration means, beam transport means, irradiation field formation means, and rotation means for rotating the particle beam circular acceleration means, the beam transport means, and the irradiation field formation means in one piece, and the acceleration orbit plane of the particle beam circular acceleration means is placed at right angles to the rotation shaft of the rotation means. Thus, the axial symmetry of the magnetic field distribution of the cyclotron is not disturbed by the components of the rotation shaft, and radiations of high-speed neutrons, etc., produced due to imbalance of the particle beam orbit can be reduced.

In the particle beam irradiation apparatus of the invention, the particle beam circular acceleration means and the rotation means are placed so that the axis of the particle beam circular acceleration means and the center line of the rotation means become coaxial. Thus, change in magnetic balance caused by rotation of the particle beam circular acceleration means and the components of the rotation means is prevented and radiations of high-speed neutrons, etc., produced due to imbalance of the orbit of the particle beam circular acceleration means can be reduced.

In the particle beam irradiation apparatus of the invention, an extension in an emission direction of the irradiation field formation means is placed so as to cross an extension to the rotation shaft of the rotation means for rotating the particle beam circular acceleration means, the beam transport means, and the irradiation field formation means. Thus, even if the irradiation direction is changed by rotation and the irradiated body is irradiated with a particle beam, the beam does not miss the target.

In the particle beam irradiation apparatus of the invention, a rotation frame is disposed at three places of both end faces of the particle beam circular acceleration means and a portion of the irradiation field formation means, so that the entire system is well balanced in load and assembly of the system is also facilitated.

In the particle beam irradiation apparatus of the invention, a radiation shield is placed between the particle beam circular acceleration means and an irradiation room, so that the radiation emitted from the particle beam circular acceleration means does not enter the irradiation room in which an irradiated body is placed, and the adverse effect of the radiation on the irradiated body can be suppressed.

In the particle beam irradiation apparatus of the invention, the rotation shield placed between the particle beam circular acceleration means and the irradiation room is placed axially symmetrically with respect to the axis of the particle beam circular acceleration means. Thus, the magnetic fields of the particle beam circular acceleration means are not disturbed and the leakage amount of radiations such as high-speed neutron beams from the particle beam circular acceleration means can be suppressed.

In the particle beam irradiation apparatus of the invention, the radiation shield placed between the particle beam circular acceleration means and the irradiation room is a composite shield comprising a nonmagnetic material and a magnetic material laminated on each other with the nonmagnetic material placed on the side of the particle beam circular acceleration means and the magnetic material on the side of the irradiation room, and the magnetic material is apart from the particle beam circular acceleration means, whereby the electromagnetic mechanical force acting between the shields and the coils can be decreased.

In the particle beam irradiation apparatus of the invention, the shield placed between the particle beam circular acceleration means and the irradiation room is a composite shield comprising a radiation shield and a magnetic material laminated on each other with the radiation shield placed on the side of the particle beam circular acceleration means and the magnetic material on the side of the irradiation room and a portion of the radiation shield larger than the outer diameter of the particle beam circular acceleration means is thinned. Thus, the electromagnetic mechanical force acting between the shields and the coils is decreased, the shields are lightened, and the rotation frame can be rotated smoothly.

In the particle beam irradiation apparatus of the invention, a composite shield comprising a magnetic material and a radiation shield laminated on each other is placed on both side faces of the irradiation room side of the particle beam circular acceleration means and the opposite side thereto with the magnetic material placed on the side of the particle beam circular acceleration means. Thus, the electromagnetic mechanical force acting between the particle beam circular acceleration means and the magnetic body is canceled between the magnetic bodies on both side faces of the particle beam circular acceleration means, so that the particle beam circular acceleration means becomes mechanically stable.

In the particle beam irradiation apparatus of the invention, a composite shield comprising a magnetic material and a radiation shield laminated on each other is placed on both side faces of the irradiation room side of the particle beam circular acceleration means and the opposite side thereto and thickness between a portion exceeding the diameter of the particle beam circular acceleration means and the outer periphery is thinned. Thus, the system is lightened and the drive force of the rotation portion can be lessened.

In the particle beam irradiation apparatus of the invention, the shield placed on both side faces of the irradiation room side of the particle beam circular acceleration means and the opposite side thereto is a composite laminated shield comprising a radiation shield sandwiched between two magnetic material layers. Thus, the allowance angle from the radiation generation source becomes large, and the radiation shields can be thinned as compared with shielding at a distant place. Since dual magnetic materials between which the radiation shield is sandwiched are used, the shielding effect of external magnetic fields can be raised as compared with single shielding.

In the particle beam irradiation apparatus of the invention, the shield placed on both side faces of the irradiation room side of the particle beam circular acceleration means and the opposite side thereto is a composite shield comprising a magnetic material and radiation shields different in material selected so that the thickness becomes the minimum in response to the radiation type, laminated on each other with the magnetic material placed so as to face the side of the particle beam circular acceleration means. Thus, the shields can be thinned, so that the system can be lightened.

In the particle beam irradiation apparatus of the invention, the particle beam circular acceleration means has magnetic field generation means formed of superconducting coils, the superconducting coils being filled with no liquefied refrigerant and cooled only by a very-low-temperature refrigerator. Thus, a device for replenishing liquid helium becomes unnecessary, leading to a simple configuration of the system, and an intricate job for replenishing liquid helium also becomes unnecessary, providing simply configured particle beam circular acceleration means.

In the particle beam irradiation apparatus of the invention, the center axis of cylinders of the very-low-temperature refrigerator for cooling the superconducting coils is placed in parallel with the rotation shaft of the particle beam circular acceleration means or at least with a very-low-temperature part placed on the bottom. Thus, if the rotation part rotates, the cooling effect of the refrigerator is maintained.

In the particle beam irradiation apparatus of the invention, the magnetic field generation means of the particle beam circular acceleration means comprises a superconducting coil for generating a main magnetic field and a shielding coil being placed on the outer periphery of the superconducting coil for canceling a magnetic field leaked on the outer periphery of the superconducting coil. Thus, even if magnetic shields on the outer periphery are not used, most of the magnetic fields leaked on outer periphery are eliminated and the magnetic shields become unnecessary, leading to a light system.

In the particle beam irradiation apparatus of the invention, the magnetic field generation means of the particle beam circular acceleration means comprises a superconducting coil for generating a main magnetic field, a shielding coil being placed on the outer periphery of the superconducting coil for canceling a magnetic field leaked on the outer periphery of the superconducting coil, and a magnetic body placed on the outer periphery of the shielding coil. Thus, particle beam circular acceleration means with no magnetic field leaked on the outer periphery is provided by the magnetic shields on the outer periphery.

In the particle beam irradiation apparatus of the invention, the superconducting coil is formed of a superconducting coil, whereby no power supply is required for the shielding coils and the shielding coils are also housed in the same vessel as the main coils, so that light particle beam circular acceleration means can be provided.

In the particle beam irradiation apparatus of the invention, an extension in the direction opposite to the travel direction of a particle beam taken out from the particle beam circular acceleration means crosses the rotation shaft of the rotation means. Thus, even if the irradiation field formation means rotates around an irradiated body and changes in position, the irradiated body can always be irradiated with beams of the same quality.

In the particle beam irradiation apparatus of the invention, the particle beam circular acceleration means comprises magnetic field generation means and high-frequency voltage application means for circularly accelerating the particle beam, an emission mechanism for taking out the accelerated particle beam, a beam focusing magnet for focusing the particle beam, and a dispersion function correction magnet, wherein the dispersion function at the exit of the particle beam and the value resulting from differentiating the dispersion function on beam travel direction coordinates become almost zero. Thus, a magnet for no dispersion in the beam transport channel after exiting the particle beam circular acceleration means becomes unnecessary and a compact system can be provided.

The particle beam irradiation apparatus comprises rotary particle beam irradiation means comprising particle beam circular acceleration means, beam transport means, irradiation field formation means, and means for rotating the particle beam circular acceleration means, the beam transport means, and the irradiation field formation means in one piece, and a plurality of fixed irradiation rooms comprising fixed beam transport means that can be connected to the beam transport means of the rotary particle beam irradiation means and fixed irradiation field formation means for forming the particle beam to any desired shape and irradiating an irradiated body with the particle beam. Thus, the availability of the particle beam irradiation apparatus can be raised.

In the particle beam irradiation apparatus of the invention, the particle beam circular acceleration means is a cyclotron or synchrocyclotron, so that a particle beam is accelerated smoothly and the target can be irradiated with the particle beam good in quality.

What is claimed is:

1. A particle beam irradiation apparatus comprising:
   particle beam circular acceleration means having particle beam generation means for generating a particle beam, said particle beam circular acceleration means generating a magnetic field through which the generated particle beam is accelerated, circularly accelerating the particle beam, and emitting a resultant particle beam;
   beam transport means for transporting the particle beam to an irradiation room in which an irradiated body is placed;
   irradiation field formation means for forming the particle beam to any desired shape and irradiating the irradiated body with the particle beam; and
   means for rotating said particle beam circular acceleration means, said beam transport means, and said irradiation field formation means as a unit,
   wherein an acceleration orbit plane, containing the circular paths along which said particle beam is accelerated, of said particle beam circular acceleration means is disposed at right angles to a rotation axis of said rotation means, and wherein
   the irradiated body to be irradiated with the particle beam is placed on the rotation axis of said rotation means.

2. The particle beam irradiation apparatus as claimed in claim 1, wherein said particle beam circular acceleration means and said rotation means are placed so that an axis of said particle beam circular acceleration means and a center line of said rotation means become coaxial.

3. The particle beam irradiation apparatus as claimed in claim 1, wherein an extension in an emission direction of said irradiation field formation means for irradiating the irradiated body with the particle beam emitted from said particle beam circular acceleration means and transported via said beam transport means is placed so as to cross an extension to the rotation shaft of said rotation means.

4. The particle beam irradiation apparatus as claimed in claim 1, wherein a rotation frame of said rotation means for rotating said particle beam circular acceleration means, said beam transport means, and said irradiation field formation means in one piece is disposed at three places of both end faces of said particle beam circular acceleration means and a portion of said irradiation field formation means.

5. The particle beam irradiation apparatus as claimed in claim 1, wherein a shield for shielding a radiation is placed between said particle beam circular acceleration means and the irradiation room in which an irradiated body is placed.

6. The particle beam irradiation apparatus as claimed in claim 5, wherein the shield placed between said particle beam circular acceleration means and the irradiation room is placed axially symmetrically with respect to the axis of said particle beam circular acceleration means.

7. The particle beam irradiation apparatus as claimed in claim 6, wherein the radiation shield placed between said particle beam circular acceleration means and the irradiation room is a composite shield comprising a nonmagnetic material and a magnetic material laminated on each other with the nonmagnetic material placed on a side of said particle beam circular acceleration means and the magnetic material on a side of the irradiation room.

8. The particle beam irradiation apparatus as claimed in claim 6, wherein the shield placed between said particle beam circular acceleration means and the irradiation room is a composite shield comprising a radiation shield and a magnetic material laminated on each other with the radiation shield placed on a side of said particle beam circular acceleration means and the magnetic material on a side of the irradiation room and wherein a portion of the radiation shield larger than an outer diameter of said particle beam circular acceleration means is thinned.

9. The particle beam irradiation apparatus as claimed in claim 1, wherein a composite shield comprising a magnetic material and a radiation shield laminated on each other is placed on both side faces of an irradiation room side of said particle beam circular acceleration means and an opposite side thereto with the magnetic material placed on a side of said particle beam circular acceleration means.

10. The particle beam irradiation apparatus as claimed in claim 1, wherein said particle beam circular acceleration means has magnetic field generation means formed of superconducting coils, said superconducting coils being cooled only by a very-low-temperature refrigerator.

11. The particle beam irradiation apparatus as claimed in claim 10, wherein a center axis of cylinders of the very-low-temperature refrigerator for cooling the superconducting coils is placed in parallel with the rotation shaft of said particle beam circular acceleration means or at least with a very-low-temperature part placed on a bottom.

12. The particle beam irradiation apparatus as claimed in claim 1, wherein the magnetic field generation means of said particle beam circular acceleration means comprises a superconducting coil for generating a main magnetic field and a shielding coil being placed on an outer periphery of said superconducting coil for canceling a magnetic field leaked on the outer periphery of said superconducting coil.

13. The particle beam irradiation apparatus as claimed in claim 1, wherein the magnetic field generation means of said particle beam circular acceleration means comprises a superconducting coil for generating a main magnetic field, a shielding coil being placed on an outer periphery of said superconducting coil for canceling a magnetic field leaked on the outer periphery of said superconducting coil, and a magnetic body placed on an outer periphery of said shielding coil.

14. The particle beam irradiation apparatus as claimed in claim 12, wherein said superconducting coil is formed of a superconducting coil.

15. The particle beam irradiation apparatus as claimed in claim 13, wherein said superconducting coil is formed of a superconducting coil.

16. The particle beam irradiation apparatus as claimed in claim 1, wherein an emission direction of a particle beam taken out from said particle beam circular acceleration means is adjusted so as to become a direction along an extension to a line connecting an emission position and a center of said particle beam circular acceleration means.

17. The particle beam irradiation apparatus as claimed in claim 1, wherein said particle beam circular acceleration means comprises:
   magnetic field generation means and high-frequency voltage application means for circularly accelerating the particle beam;
   an emission mechanism for outputting the accelerated particle beam;
   and a dispersion function correction magnet,
   wherein a dispersion function of the particle beam at an output thereof and a value resulting from differentiating the dispersion function in a beam travel direction become almost zero.

18. The particle beam irradiation apparatus as claimed in claim 1, wherein said particle beam circular acceleration means is a cyclotron or synchrocyclotron.

19. A particle beam irradiation apparatus comprising:
(1) rotary particle beam irradiation means comprising: particle beam circular acceleration means having particle beam generation means for generating a particle beam, said particle beam circular acceleration means generating a magnetic field through which the generated particle beam is accelerated, circularly accelerating the particle beam, and emitting a resultant particle beam; beam transport means for transporting the accelerated particle beam; irradiation field formation means for forming the particle beam into any desired shape and irradiating a first irradiated body with the particle beam; and means for rotating said particle beam circular acceleration means, said beam transport means, and said irradiation field formation means as a unit; wherein said first irradiated body is placed in a rotary irradiation room accommodating said first irradiated body on the rotation axis of said rotation means; and
(2) at least one fixed irradiation room, each comprising: fixed beam transport means that can be connected to said beam transport means of said rotary particle beam irradiation means; and fixed irradiation field formation means for forming the particle beam into any desired shape and irradiating a second irradiated body, placed within said at least one fixed irradiation room, with the particle beam.

20. The particle beam irradiation apparatus as claimed in claim 19 wherein said particle beam circular acceleration means is a cyclotron or synchrocyclotron.

21. The particle beam irradiation apparatus as claimed in claim 19 wherein said fixed beam transport means is disposed outside a room containing said first irradiated body.

22. A particle beam irradiation apparatus comprising:
(1) rotary particle beam irradiation means comprising: particle beam circular acceleration means having particle beam generation means for generating a particle beam, said particle beam circular acceleration means generating a magnetic field through which the generated particle beam is accelerated, circularly accelerating the particle beam, and emitting a resultant particle beam; beam transport means for transporting the accelerated particle beam; irradiation field formation means for forming the particle beam to any desired shape and irradiating a first irradiated body with the particle beam; and means for rotating said particle beam circular acceleration means, said beam transport means, and said irradiation field formation means as a unit; wherein said first irradiated body is placed in a rotary irradiation room accommodating said first irradiated body on the rotation axis of said rotation means; and
(2) at least one fixed irradiation room comprising: fixed beam transport means that can be connected to said beam transport means of said rotary particle beam irradiation means; and fixed irradiation field formation means for forming the particle beam into any desired shape and irradiating a second irradiated body, placed within said at least one fixed irradiation room, with the particle beam,
wherein an acceleration orbit plane, containing the circular paths along which said particle beam is accelerated, of said particle beam circular acceleration means is disposed at right angles to a rotation axis of said rotation means.

23. The particle beam irradiation apparatus as claimed in claim 22 wherein said particle beam circular acceleration means is a cyclotron or synchrocyclotron.

* * * * *